United States Patent
McClure et al.

(10) Patent No.: US 6,625,490 B1
(45) Date of Patent: Sep. 23, 2003

(54) SYSTEM AND METHOD OF AUTOMATICALLY ADJUSTING SENSING PARAMETERS BASED ON TEMPORAL MEASUREMENT OF CARDIAC EVENTS

(75) Inventors: Kelly H. McClure, Simi Valley, CA (US); Gene A. Bornzin, Simi Valley, CA (US); Junyu Mai, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 133 days.

(21) Appl. No.: 09/992,739

(22) Filed: Nov. 14, 2001

(51) Int. Cl.$^7$ .............................................. A61N 1/362
(52) U.S. Cl. ............................................................ 607/9
(58) Field of Search ...................................... 607/4–28

(56) References Cited

U.S. PATENT DOCUMENTS

| | | | |
|---|---|---|---|
| 4,708,144 A | 11/1987 | Hamilton et al. | 128/419 PG |
| 4,766,902 A | 8/1988 | Schroeppel | 128/419 PG |
| 4,768,511 A | 9/1988 | DeCote, Jr. | 128/419 PG |
| 5,413,592 A | 5/1995 | Schroeppel | 607/18 |
| 5,466,254 A | 11/1995 | Helland | 607/123 |
| 5,522,855 A | 6/1996 | Hoegnelid | 607/9 |
| 5,534,016 A | 7/1996 | Boute | 607/9 |
| 5,564,430 A | 10/1996 | Jacobson et al. | 128/697 |
| 5,591,214 A | 1/1997 | Lu | 607/9 |
| 5,674,254 A | 10/1997 | van Krieken | 607/11 |
| 5,735,881 A | 4/1998 | Routh et al. | 607/14 |
| 5,755,738 A | 5/1998 | Kim et al. | 607/9 |
| 5,782,888 A | 7/1998 | Sun et al. | 607/27 |
| 5,861,009 A | 1/1999 | Armstrong et al. | 607/17 |
| 5,913,880 A | 6/1999 | Vonk | 607/27 |

*Primary Examiner*—Scott M. Getzow

(57) ABSTRACT

A system and method for automatically adjusting the sensing parameters in an implantable cardiac stimulation device is described. The adjustment is based on the amplitudes and the onsets and ends of cardiac events, such as R-waves, T-waves, far-field R-waves, and/or far-field T-waves. Having determined the onset and termination of the cardiac events for a given number of cardiac cycles, particular variables that characterize these cardiac events can be averaged and stored in memory. Such variables include the peak amplitudes sampled during a cardiac event, the duration of the cardiac event, and the duration between cardiac events. Based on the averaged variables, the system automatically adjusts the sensing parameters, such as sensitivity, and blanking and refractory periods.

33 Claims, 15 Drawing Sheets

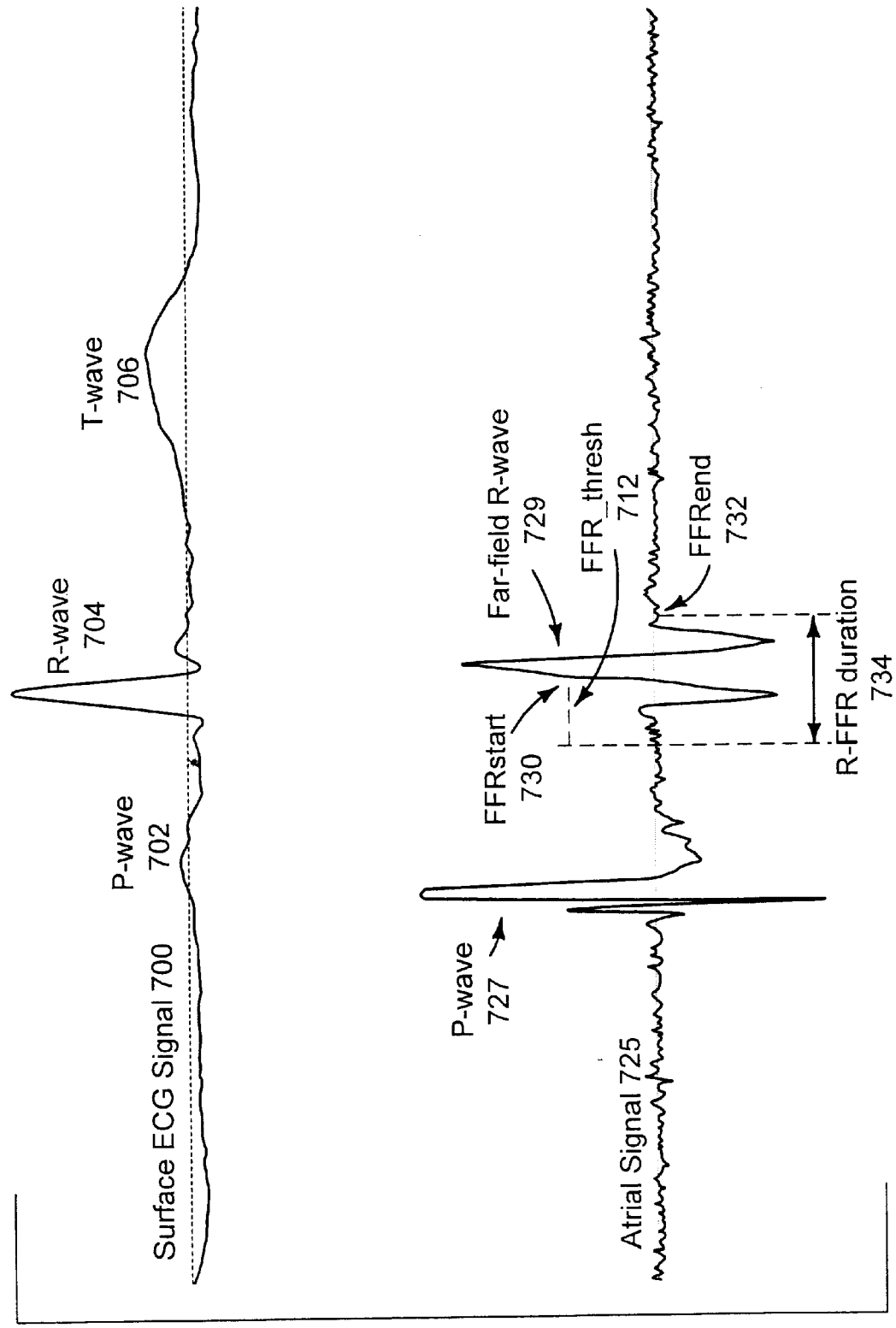

SYSTEM AND METHOD OF AUTOMATICALLY ADJUSTING SENSING PARAMETERS BASED ON TEMPORAL MEASUREMENT OF CARDIAC EVENTS

CROSS-REFERENCE TO RELATED APPLICATIONS

This application is related to copending U.S. application Ser. No. 09/354,244, titled "System and Method for Automatically Adjusting Sensitivity in an Implantable Cardiac Stimulation Device", filed on Jul. 15, 1999, which is incorporated herein by reference in its entirety. This application is also related to U.S. application Ser. No. 09/992,740, titled "System and Method of Automatically Determining the Onsets and Ends of Cardiac Events and Far-Field Signals," filed concurrently herewith.

FIELD OF THE INVENTION

The present invention relates generally to implantable medical devices and methods, and particularly to a system and associated method for use with an implantable stimulation device, such as a pacemaker or a cardioverter-defibrillator device (ICD), to automatically adjust sensing parameters based on temporal measurement of cardiac signals. More specifically, the adjustment of the sensing parameters is based on temporal measurements of the onsets and ends of cardiac events such as R-waves and T-waves, and/or far-field signals such as far-field R-waves and far-field T-waves.

BACKGROUND OF THE INVENTION

Conventional pacemakers and ICDs require manual programming of numerous programmable parameters including but not limited to: ventricular sensitivity, atrial sensitivity, post-ventricular atrial refractory period (PVARP), post-ventricular atrial blanking period (PVAB), ventricular refractory period (VREF), and other parameters such as ventricular output, atrial output, choice of pacing mode, upper rate limit, base rate, sleep rate, sensor slope, sensor threshold, and so forth. The programming of these parameters can be inaccurate and time consuming, and requires highly-skilled medical expertise to accomplish. Attempts to automate the programming of these parameters have not been completely successful, in part because of the inaccuracy of determining the onsets and ends of cardiac events such as P-waves, R-waves and T-waves, and far-field signals such as far-field R-waves and far-field T-waves.

For example, when sensing in the atrium, PVAB is a key parameter in the correct performance of automatic mode switching, in that an incorrectly short PVAB would result in atrial over-sensing and inappropriate mode switching, and an overly long PVAB would prevent the correct detection of atrial fibrillation and would result in inappropriate ventricular pacing during atrial fibrillation, with serious hemodynamic consequences. In addition, under-sensing of premature atrial contractions (PACs) and premature ventricular contractions (PVCs) can result in arrhythmia induction.

Therefore, there is a great and still unsatisfied need for a system and method which not only discriminate between sensed cardiac events such as P-waves, R-waves and T-waves, and far-field signals such as far-field R-waves and far-field T-waves, but which will also automatically and accurately determine the onsets and ends of these events and signals.

The problem of automatically and accurately sensing P-waves, R-waves, and T-waves is even more pronounced when using an "A-V combipolar" electrode configuration, that is, an electrode configuration in which the stimulation device senses cardiac signals between an atrial tip electrode and a ventricular tip electrode, and stimulates each chamber in a unipolar fashion from the respective electrode to the housing (i.e., typically referred to as the case electrode). For a more complete description of combipolar systems, see U.S. Pat. No. 5,522,855 (Hognelid), which reference is incorporated herein by reference. When such electrodes are implanted, various electrode sensing configurations are possible, e.g., atrial unipolar (A tip-case); ventricular unipolar (V tip-case); atrial-ventricular combipolar (A tip-V tip); ventricular unipolar ring (V ring-case) or atrial unipolar ring (A ring-case).

More specifically, regardless of the cardiac event being sensed, and regardless of the electrode configuration being used, there is a need for an implantable device that is able to readily and reliably distinguish between P-waves, R-waves and T-waves. This is because the implantable device, if it is to perform its intended function, must know when an atrial depolarization (P-wave) occurs, and when a ventricular depolarization (R-wave) occurs, and it must not falsely sense a T-wave or noise as a P-wave or R-wave.

For example, it is of critical importance that the implantable device be capable of recognizing the occurrence of certain atrial arrhythmias based on the sensed atrial rate, and in determining such rate it is critically important that neither far field R-waves nor far field T-waves be falsely sensed as a P-wave. Such may be particularly noticeable when an A-V combipolar electrode configuration is being used because, in such configuration, P-waves, R-waves, and T-waves may be sensed as being of the same order of magnitude.

While it is well known that various blanking schemes may be used to block or blank out unwanted T-waves and retrograde P-waves by using different blanking intervals (i.e., PVARP, automatic PVARP extension, PVAB, etc.), and thereby prevent these T-waves or retrograde P-waves from being falsely sensed as P-waves, such blanking schemes (based solely on timing considerations) have proven less than satisfactory because legitimate (antegrade) P-waves and PVCs that need to be sensed, may and do occur during these blanking intervals.

Differentiation schemes based on the morphology of the sensed waveform have also been used. These schemes are premised on the fact that P-waves, R-waves and T-waves have inherently different shapes. Thus, in theory, all one needs to do is to examine the morphology of the sensed waveform. Unfortunately, morphology-based schemes require that the entire waveform be captured and analyzed, a process that not only requires waiting until the entire waveform has occurred, but also may require significant on-chip processing capability and processing time.

Thus, it is seen that there is a need in the implantable cardiac stimulator art to automatically and accurately detect, discriminate, and determine the onsets and ends of cardiac events such as P-waves, R-waves and T-waves, and far-field signals such as far-field R-waves and far-field T-waves, without relying solely on blanking considerations or morphology. This need becomes particularly acute when sensing between intra-chamber electrodes, e.g., when sensing using an A-V combipolar electrode configuration.

Thus, it is seen that there is a need for an implantable cardiac stimulator that automatically and accurately detects, discriminates, and determines the onsets and ends of cardiac events such as R-waves and T-waves, and far-field signals such as far-field R-waves and far-field T-waves, without relying solely on blanking considerations or morphology.

SUMMARY OF THE INVENTION

The present invention addresses these problems by providing a system and method for automatically determining the onset and termination of cardiac events, namely the R-wave, the T-wave and the far-field signals sensed in the atria associated with the R-wave, commonly referred to as the far-field R-wave (FFR) and T-wave, commonly referred to as the far-field T-wave (FFT). Furthermore, having determined the temporal location and duration of these events as well as their peak amplitudes, the present invention provides a method for automatically setting various pacemaker parameters, specifically PVAB, PVARP, VREF, atrial sensitivity, and ventricular sensitivity.

In one embodiment a method of automatically adjusting a cardiac sensing parameter is described, in which the occurrence of a cardiac signal is sensed, and the sensed cardiac signal is sampled. An onset and an end of the sensed cardiac signal is determined from the samples, as is the duration and amplitude of the cardiac signal. Finally, if the stability of the cardiac signal is verified, the cardiac sensing parameter is calculated based on the duration and amplitude of the cardiac signal.

BRIEF DESCRIPTION OF THE DRAWINGS

The above and further features, advantages and benefits of the present invention will be apparent upon consideration of the following detailed description, taken in conjunction with the accompanying drawings, in which like reference characters refer to like parts throughout, and in which:

FIG. 6 is depicted in two parts wherein:

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

As indicated earlier, the present invention is directed at providing a method for reliably and accurately detecting the onsets and ends of cardiac events sensed in the atria and/or in the ventricles by an implanted cardiac stimulation device. While the methods of the present invention could be implemented in numerous implantable cardiac stimulation devices including pacemakers, cardioverters or defibrillators, or any combination thereof, for the sake of convenience, the description of one implantable cardiac stimulation device is provided in conjunction with FIGS. 1 and 2, in which one embodiment of the present invention may be implemented as will be described in detail in conjunction with FIGS. 3 through 8.

Figure 1:
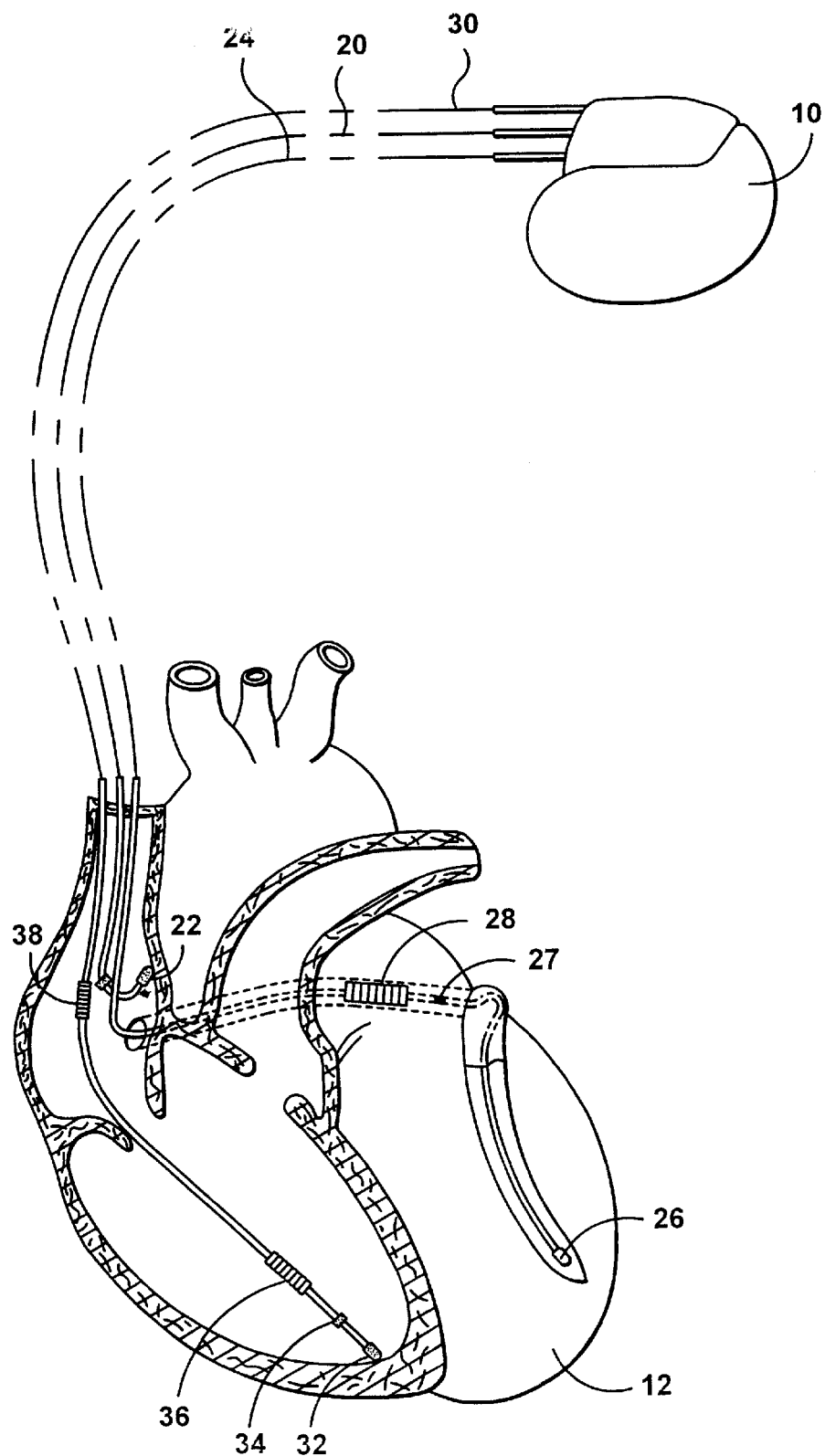
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, entitled "Coronary Sinus Lead with Atrial Sensing Capability" (Helland), which patents are hereby incorporated herein by reference. The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC (superior vena cava) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
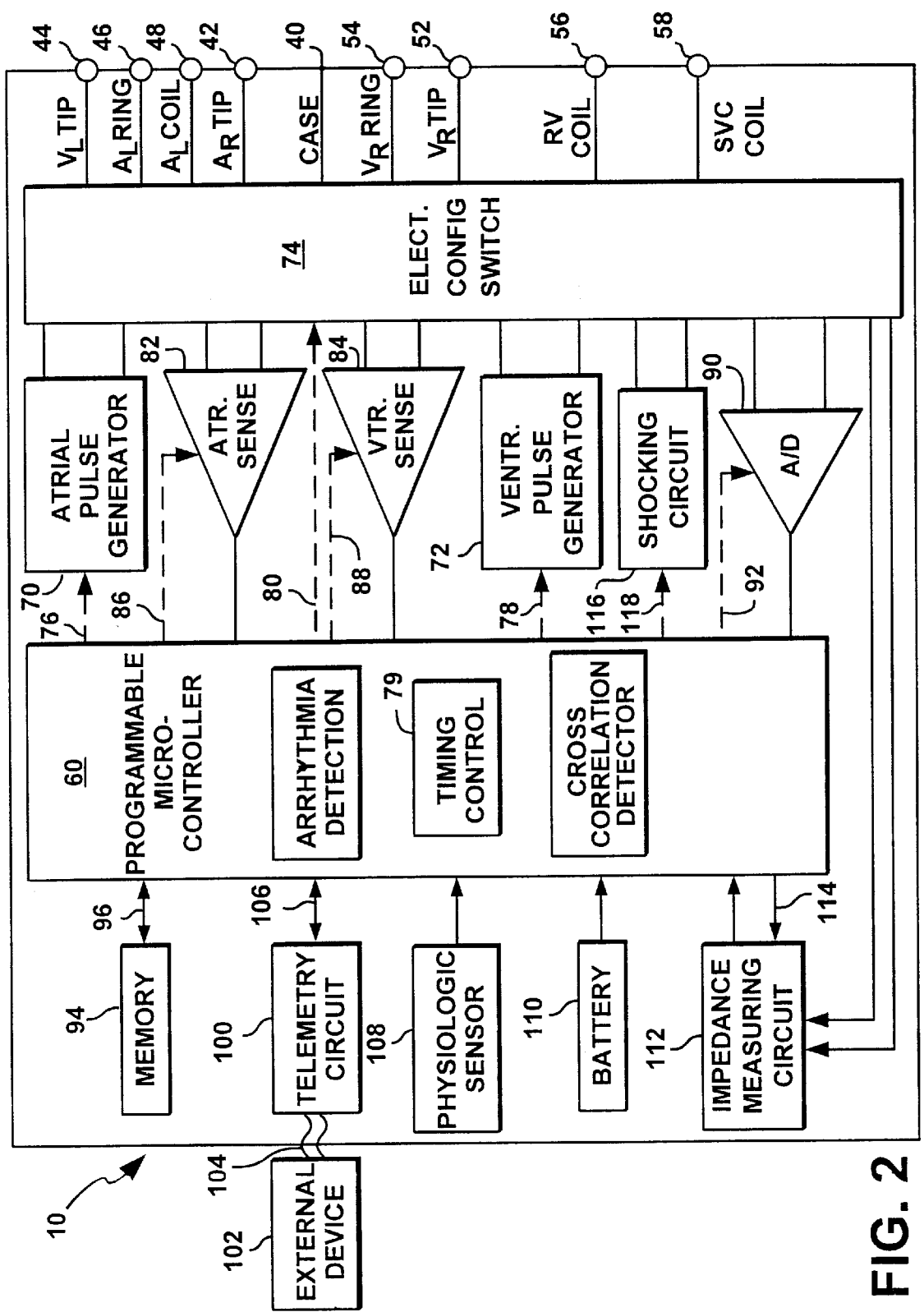
FIG. 2 is a functional block diagram of the multi-chamber implantable stimulation device of FIG. 1, illustrating the basic elements that provide cardioversion, defibrillation and/or pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 comprises a housing 40 which is often referred to as "can", "case" or "case electrode", and which may be programmably selected to act as the return electrode for all "unipolar" modes. The housing 40 may further be used as a return electrode alone or in combination with one or more of the coil electrodes, 28, 36 and 38, for shocking purposes. The housing 40 further comprises a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector comprises at least a right atrial tip terminal ($A_R$ TIP) 42 adapted for connection to the atrial tip electrode 22.

To achieve left chamber sensing, pacing and shocking, the connector comprises at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial tip electrode 27, and the left atrial coil electrode 28, respectively.

To support right chamber sensing, pacing and shocking, the connector further comprises a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically comprises a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 comprises the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further comprises timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 comprises a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88,from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the stimulation device 10 is the ability to sense and store a relatively large amount of data (e.g. from the data acquisition system 90), which data may then be used for subsequent analysis to guide the programming of the stimulation device 10.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through an established communication link 104.

In a preferred embodiment, the stimulation device 10 further comprises a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

While the physiologic sensor 108 is shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, pressure, cardiac output, ejection fraction, stroke volume, end diastolic volume, end systolic volume, respiration rate and/or minute ventilation, pH of blood, ventricular gradient, etc. However, any sensor may be used which is capable of sensing a physiological parameter that corresponds to the exercise state of the patient.

The stimulation device additionally comprises a battery 110 which provides operating power to all of the circuits shown in FIG. 2. For the stimulation device 10, which employs shocking therapy, the battery 110 must be capable of operating at low current drains for long periods of time (preferably less than 10 $\mu$A), and then be capable of providing high-current pulses (for capacitor charging) when the patient requires a shock pulse (preferably, in excess of 2 A, at voltages above 2 V, for periods of 10 seconds or more). The battery 110 must preferably have a predictable discharge characteristic so that elective replacement time can be detected. Accordingly, the stimulation device 10 preferably employs lithium/silver vanadium oxide batteries.

The stimulation device 10 further comprises a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 via a control signal 114. Certain applications for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the heart valves, etc. The impedance measuring circuit 112 is advantageously coupled to the switch 74 so that any desired electrode may be used.

In the case where the stimulation device 10 is intended to operate as an implantable cardioverter/defibrillator (ICD) device, it needs to detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38 (FIG. 1). As noted above, the housing 40 may act as an-active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In FIG. 3, a flow chart is shown describing an overview of the operation and novel features implemented in one embodiment of the stimulation device 10. In this flow chart, and the other flow charts described herein, the various algorithmic steps are summarized in individual "blocks". Such blocks describe specific actions or decisions that must be made or carried out as the algorithm proceeds. Where the microcontroller 60 (or its equivalent) is employed, the flow charts presented herein provide the basis for a "control program" that may be executed or used by such a microcontroller 60 (or its equivalent) to effectuate the desired control of the stimulation device 10. Those skilled in the art may readily write such a control program based on the flow charts and other descriptions presented herein.

In this embodiment, the control program is comprised of multiple integrated program modules, with each module bearing responsibility for controlling one or more functions of the stimulation device 10. For example, one program module may control the delivery of stimulating pulses to the heart 12, while another may control the verification of ventricular capture and ventricular pacing energy determination. In effect, each program module is a control program dedicated to a specific function or set of functions of the stimulation device 10.

In accordance with the present invention, a set of program modules will control the measurement of certain variables made possible by the accurate detection of cardiac events and, based on these measured variables, automatically adjust various sensing parameters. The stimulation device 10 may be programmed to automatically adjust any or all of the following programmable parameters relating to the sensing operations of the stimulation device 10: the atrial sensitivity; the post-ventricular atrial blanking period (PVAB); the ventricular sensitivity; the ventricular refractory period (VREF); and/or the post-ventricular atrial refractory period (PVARP).

If the atrial sensitivity and/or the post-ventricular atrial blanking period (PVAB) are programmed to be automatically adjusted, the atrial signal received by atrial sensing circuit 82 needs to be processed according to methods to be described in conjunction with FIG. 3. If the ventricular sensitivity, the ventricular refractory (VREF) and/or the post-ventricular refractory period (PVARP) are programmed to be automatically adjusted, the ventricular signal received by ventricular sensing circuit 84 needs to be processed according to methods to be described in conjunction with FIG. 4. In both cases, the cardiac signal received by atrial sensing circuit 82 or ventricular sensing circuit 84 is sampled and digitized by analog-to-digital (A/D) converter 90, and this digitized data is stored in a memory buffer of adequate capacity, within A/D converter 90, to allow processing according to the methods to be described in conjunction with FIGS. 3 and 4.

If the stimulation device 10 is programmed such that both the atrial and the ventricular signals must be processed, the signals are each processed separately, and then adjustments are made to the associated sensing parameters as necessary. For example, the stimulation device 10 may process the atrial signal and adjust the atrial sensitivity and post-ventricular atrial blanking period (PVAB) first, and then process the ventricular signal and adjust the ventricular sensitivity, the ventricular refractory period (VREF) and the post-ventricular atrial refractory period (PVARP) second. The order of which signal, atrial or ventricular, is processed first is not critical to the operation of the present invention.

The operations for processing atrial and/or ventricular signals and adjusting sensing parameters may be triggered to occur periodically, as programmed by the physician (for example, every two hours, eight hours, 24 hours, etc.) according to the patient's need, or these operations may be programmed to run continuously such that sensing parameters are continuously adjusted and updated according to fluctuations in cardiac function.

In FIG. 3, a method 200 by which the device 10 processes the atrial signal is illustrated. The method 200 is employed by the device 10 to automatically and reliably detect far-field R-waves (FFR) and far-field T-waves (FFT) by precisely determining the onsets and ends of these waves. Generally, the method 200 identifies, in sequence, the onset of the far-field R-wave, the end of the far-field R-wave, the onset of the far-field T-wave, and the end of the far-field T-wave during one cardiac cycle, all of which may be associated with either an intrinsic depolarization occurring in the ventricle or a ventricular evoked response due to a pacing pulse delivered in the ventricle.

For purposes of simplifying the following description, the use of the term "ventricular event" is intended to include all ventricular events, whether intrinsic or evoked responses. Further, the term far-field R-wave (FFR) is construed to cover all far-field R-waves, whether they are associated with intrinsic R-waves or evoked responses in the ventricle, since the processing is generally the same for both, and may only differ by a constant or an offset. Likewise, the term far-field T-wave (FFT) refers to all far-field T-waves, whether they are associated with intrinsic or evoked responses in the ventricle.

In practice, however, the methods of FIGS. 3 and 4 may be adapted to keep track of the ventricular paced events and the ventricular sensed events, and to provide two sets of sensing parameter settings (i.e., atrial sensitivity, ventricular sensitivity, VREF, PVARP and PVAB): one set to be implemented during ventricular pacing (or stimulation) and one set during ventricular sensing. Thus, in method 200 of FIG. 3, the measured parameters related to the onset and the termination of the far-field R-wave and the far-field T-wave detected in the atrial channel during ventricular sensing will be saved separately from the measurements of these same parameters measured during ventricular pacing. The measured parameters during ventricular sensing and the measured parameters during ventricular pacing will then be used to adjust the sensing parameters to be applied during episodes of ventricular sensing and ventricular pacing, respectively.

Method 200 starts at step 202 by initializing the settings for atrial sensitivity and post-ventricular atrial blanking (PVAB). These settings can assume the values programmed by the physician; default values stored in memory 94; or the last effective settings if this is not the first time that method 200 has been enabled. At step 204, method 200 waits for a ventricular event (R-wave) to be detected by the ventricular sensing circuit 84. If no ventricular event is detected within a pre-defined period of time, method 200 keeps waiting for a ventricular event by looping back to step 204 until a ventricular event does occur.

Once a ventricular event is detected, the time at which the R-wave begins (Rstart) is recorded in memory 94 at step 206. This time corresponds to the first digitized sample point, obtained from the ventricular signal received by the ventricular sensing circuit 84 and digitized by the A/D converter 90, that equals or exceeds a defined R-wave threshold, preferably equal to the programmed ventricular sensitivity.

At step 208, method 200 searches the atrial signal received by the atrial sensing circuit 82 for the onset of the far-field R-wave (FFR) associated with the R-wave detected at step 204. The details by which the stimulation device 10 detects the onset of the far-field R-wave will be described later in conjunction with FIG. 5.

At decision step 210, method 200 determines if the onset of the far-field R-wave (FFR) has been detected. If not, the method 200 determines whether the onset of the far-field R-wave has not been detected for a given number of cardiac cycles, n (e.g., 2 consecutive cardiac cycles, or more), at step 212. If the answer to this inquiry is negative, method 200 returns to step 204 to await the next ventricular event and to search again for the onset of the far-field R-wave.

However, if the answer to the inquiry at step 212 is affirmative, that is if the far-field R-wave has not been detected for a given number of cardiac cycles, n, then, method 200 proceeds to decision step 214 where a determination is made as to whether the atrial sensitivity is at the highest available level. The atrial sensitivity may be too low at the existing setting to allow detection of the onset of the far-field R-wave. Thus, if the atrial sensitivity is not at the highest available level, the atrial sensitivity is increased by one programmable setting at step 216, and the method 200 returns to step 204 to attempt to detect the onset of the far-field R-wave at the new, more sensitive, atrial sensitivity setting during the next cardiac cycle. If the atrial sensitivity has reached the highest level available as determined at decision step 214, the method 200 will be terminated at step 218.

In this way, the atrial sensitivity is progressively increased until the onset of a far-field R-wave is detected or until the maximum atrial sensitivity is reached. At each atrial sensitivity setting, a n cardiac cycles are searched for the onset of the far-field R-wave before increasing the atrial sensitivity further. The number, n, of cardiac cycles searched for the onset of the far-field R-wave is preferably a programmable value, in the range of 1 to 5, though other value can also be selected.

Returning now to decision step 210 (FIG. 3A), if the onset of the far-field R-wave is detected, method 200 proceeds to step 220 to search for the end of the far-field R-wave (FFR). The details of the methods by which the stimulation device 10 searches for the end of the far-field R-wave will be described later in connection with FIG. 7.

Once the search for the end of the far-field R-wave is completed, method 200 proceeds to decision step 222 (FIG. 3B) to determine if the end of the far-field R-wave was detected. The end of the far-field R-wave may not be detected due, for example, to noise or because the atrial sensitivity is too high. If the end of the far-field R-wave is not detected, method 200 proceeds to step 224 (FIG. 3C) to determine if the end of the far-field R-wave has not been detected for a pre-defined number of consecutive cardiac cycles, n (e.g., 2 or more consecutive cardiac cycles).

If the answer to the inquiry at decision step 224 is negative, method 200 returns to step 204 (FIG. 3A) to attempt detecting the end of the far-field R-wave during the next cardiac cycle. If the answer to the inquiry at step 224 is affirmative, that is the end of the far-field R-wave has not been detected for a given number of consecutive cardiac cycles, then a determination is made as to whether the atrial sensitivity has reached the lowest available level at step 226 (FIG. 3C). If not, the atrial sensitivity is decreased by one programmable setting at step 228, and method 200 returns to step 204 (FIG. 3A) to search for the end of the far-field R-wave at the new, less sensitive, atrial sensitivity setting. If the atrial sensitivity has reached the lowest available level as determined at decision step 226, method 200 will be terminated at step 230 (FIG. 3C).

In this way, the atrial sensitivity is progressively decreased until the end of the far-field R-wave is detected or until the atrial sensitivity reaches the least sensitive setting available. At each atrial sensitivity setting, n cardiac cycles are searched for the end of the far-field R-wave before decreasing the atrial sensitivity further. The number n of cardiac cycles searched for the end of the far-field R-wave is preferably a programmable value, in the range of 1 to 5, and may or may not be equal to the number of cardiac cycles searched for the onset of the far-field R-wave.

If the end of the far-field R-wave is detected as determined at decision step 222 (FIG. 3B), method 200 proceeds to step 232 to search for the onset of the subsequent far-field T-wave (FFT), as will be described in greater detail in connection with FIG. 6B.

At decision step 234 (FIG. 3B), method 200 determines if the onset of the far-field T-wave has been detected. If it has not been detected, method 200 determines whether the onset of a far-field T-wave has not been detected for a pre-defined number of cardiac cycles, n (e.g., five cardiac cycles), at decision step 244.

If the answer to the inquiry at decision step 244 is negative, method 200 returns to step 204 (FIG. 3A) to search the next cardiac cycle for the onset of a far-field T-wave. However, if the answer to the inquiry at step 244 is affirmative, that is if method 200 has not detected the onset of a far-field T-wave for a given number, n, of cardiac cycles, method 200 will not make any further attempt to detect the far-field T-wave. Method 200 proceeds to step 246 to check the stability of the measurements made thus far, and to adjust the atrial sensitivity and post-ventricular atrial blanking period (PVAB) as appropriate. The details of step 246 for verifying measurement stability and adjusting sensing parameters will be further described in conjunction with FIG. 9.

If the onset of the far-field T-wave is detected, as determined at decision step 234, method 200 proceeds to step 236 to search for the end of the far-field T-wave. The method by which the stimulation device 10 searches for the end of the far-field T-wave will be described in greater detail in conjunction with FIG. 7.

Method 200 then proceeds to decision step 238 (FIG. 3C) to determine if the end of the far-field T-wave has been detected. If the answer to this inquiry is negative, method 200 proceeds to step 240 to determine if the end of the far-field T-wave has not been detected for a pre-defined number of cardiac cycles, n (e.g., 2 or more consecutive cardiac cycles). If the answer to this inquiry is negative, method 200 returns to step 204 (FIG. 3A) to search the next cardiac cycle for the end of the far-field T-wave.

If the answer to the inquiry at step 240 is affirmative, that is method 200 has not detected the end of the far-field T-wave for a given number of cardiac cycles, then a determination is made at step 226 (FIG. 3C) as to whether the atrial sensitivity has reached the lowest level available. The atrial sensitivity may be too high at the existing setting to allow detection of the end of the far-field T-wave. Thus, If the atrial sensitivity is not at the least sensitive setting available, it is decreased by one programmable setting at step 228, and method 200 returns to step 204 to search for the end of the far-field T-wave during the next cardiac cycle at the new, less sensitive, atrial sensitivity setting. If the atrial sensitivity has reached the lowest level available as determined at decision step 226, method 200 is terminated at step 230.

In this way, method 200 progressively decreases the atrial sensitivity until the end of the far-field T-wave is detected or until the atrial sensitivity reaches the least sensitive setting available. At each atrial sensitivity setting, n cardiac cycles are searched for the end of the far-field T-wave before decreasing the atrial sensitivity further. The number n of cardiac cycles searched for the end of the far-field T-wave is preferably a programmable value, in the range of 1 to 5, and may or may not be equal to the number of cardiac cycles searched for the onset and end of the far-field R-wave.

Figure 3A:
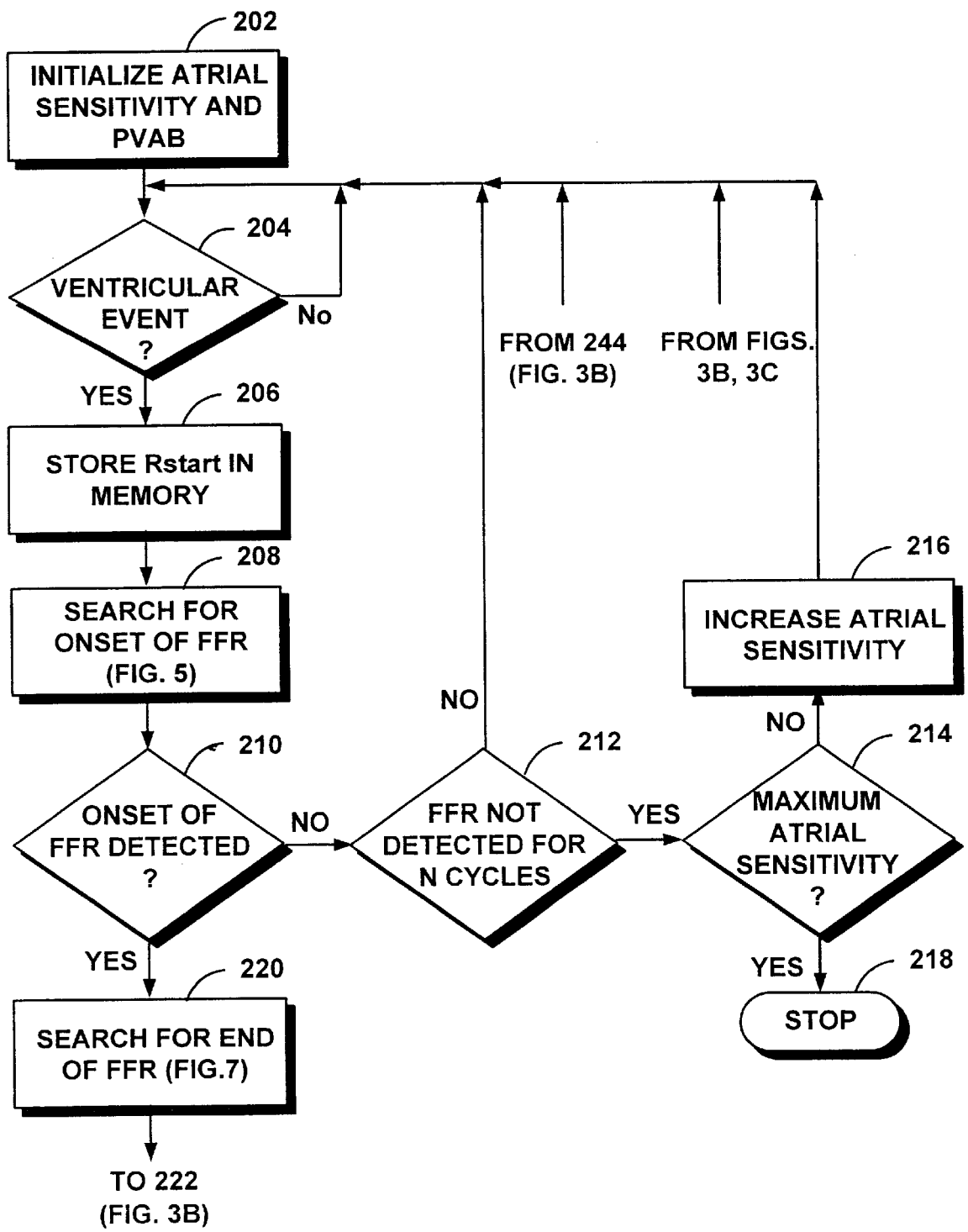
FIG. 3 is comprised of FIGS. 3A, 3B and 3C, and represents a flow diagram illustrating an overview of the operation of the stimulation device of FIGS. 1 and 2 in the atrial channel, for automatically and reliably detecting the onsets and ends of the far-field R-waves and far-field T-waves, and for adjusting sensing parameters related to the same.
Figure 3B:
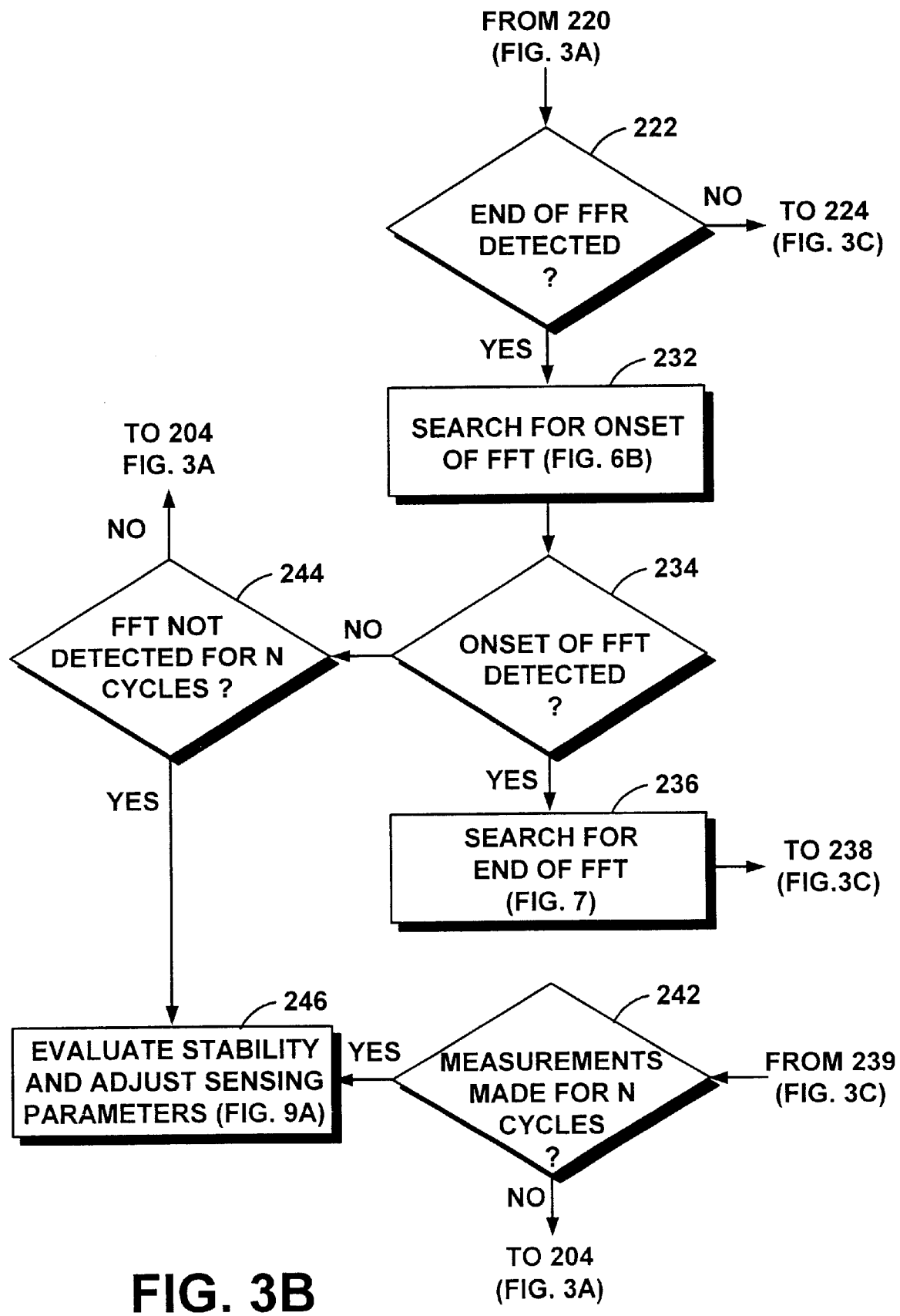
Figure 3C:
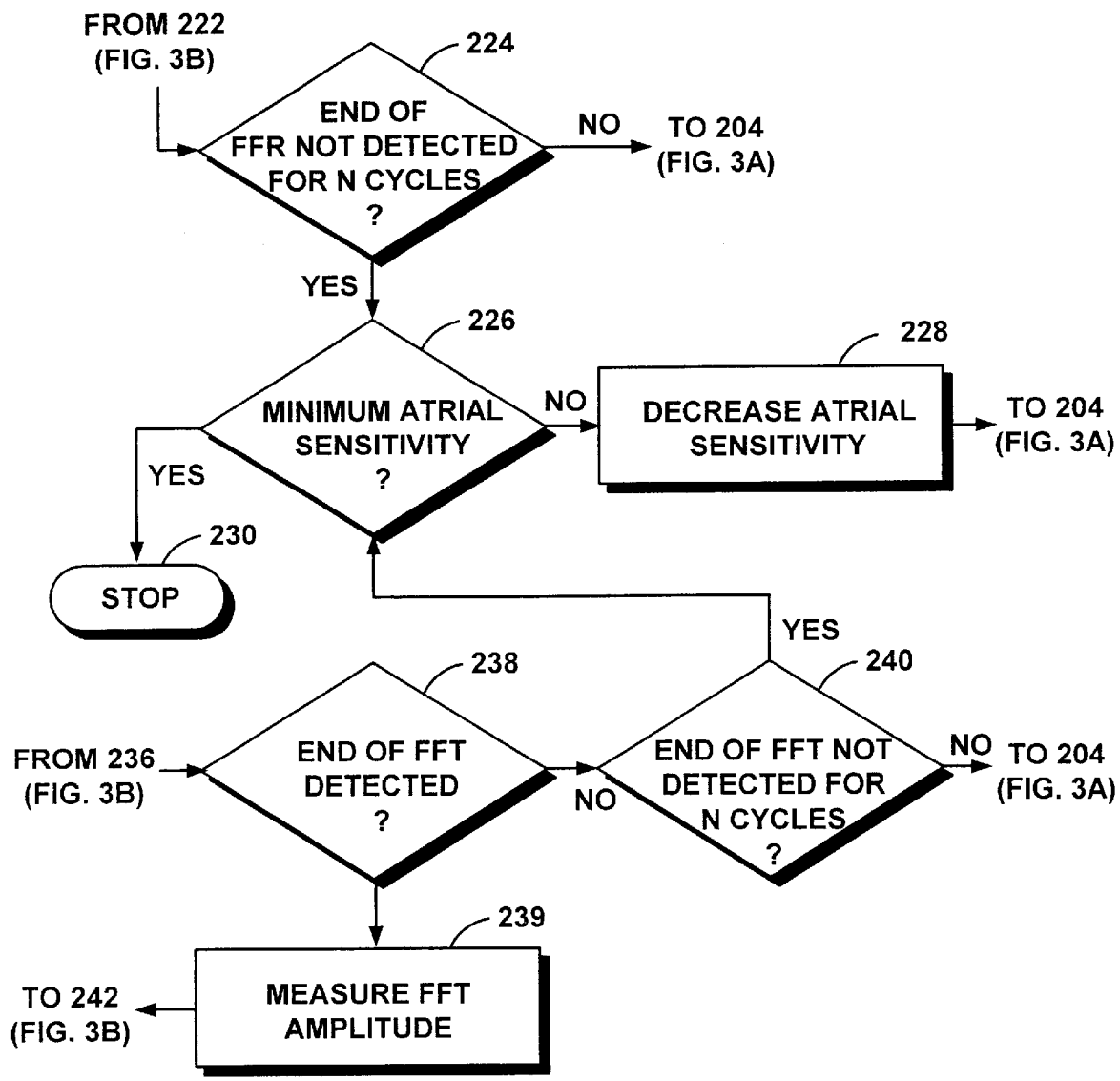

If at decision step 238 (FIG. 3C), method 200 has detected the end of the far-field T-wave, the maximum amplitude of the sampled atrial signal between the detected onset of the far-field T-wave and the detected end of the far-field T-wave will be measured and stored in memory 94 as the far-field T-wave (FFT) amplitude at step 239, and method 200 proceeds to step 242 (FIG. 3B).

At decision step 242, method 200 determines if measurements of the onset and end of the far-field R-waves and far-field T-waves have been made for a desired number of cardiac cycles, N (e.g., 5 cardiac cycles). This number, N, of cardiac cycles represents the desired number of measurements to be made in order to perform statistical analyses on the measured variables as will be done in the next step 246.

Results from the statistical analyses are used to verify measurement stability and to perform the automatic adjustments of sensing parameters as will be described in conjunction with FIG. 9. The number, N, of measurements required of each variable is preferably a programmable value ranging from 1 to 10, and more preferably 5. It should be clear that in other embodiments, the value of N can be different.

If the desired number, N, of measurements has not yet been made, method 200 is repeated, by returning to step 204 (FIG. 3A), until the desired number of measurements of the onset and end of far-field R-waves, and the onset, end and amplitude of far-field T-waves have been made and stored in memory 94. Once the desired number, N, of measurements have been collected, as determined at decision step 242 (FIG. 3B), method 200 proceeds to step 246 to evaluate the stability of these measurements and to adjust sensing parameters related to atrial sensing (atrial sensitivity and post-ventricular atrial blanking), as will be described in detail in connection with FIG. 9.

FIG. 4 illustrates a method 250 used by the stimulation device 10 to process the ventricular signal, received by the ventricular sensing circuit 84, for detecting the onset of the R-wave, the end of R-wave, the onset of the T-wave and the end of the T-wave, all of which may be associated with an intrinsic depolarization or an evoked response in the ventricle. The measured parameters related to the onset and end of R-waves and T-waves, and the corresponding intervals between these events, will be used to adjust the ventricular sensing parameters (ventricular sensitivity and ventricular refractory period) and one atrial sensing parameter, post-ventricular atrial refractory period (PVARP). Method 250 of FIG. 4 may be adapted to keep track of ventricular paced and ventricular sensed events separately so as to determine two sets of parameter settings (ventricular sensitivity, ventricular refractory period, and post-ventricular atrial refractory period): one set to be implemented during ventricular pacing and one set during ventricular sensing.

Method 250 starts at step 252 (FIG. 4A) by initializing the ventricular sensitivity, the ventricular refractory period (VREF) and the post-ventricular atrial refractory period (PVARP). These parameters may assume the values programmed by the physician, default values stored in device 10, or the last effective settings if this is not the first time that method 250 has been enabled.

At step 254, method 250 waits for a ventricular event (R-wave). If no ventricular is sensed or paced event within a predefined period of time, method 250 keeps waiting for a ventricular event by looping back to step 254. Once a ventricular event is detected, the time at which the R-wave begins (Rstart) is recorded in memory 94 at step 256. This time corresponds to the first digitized ventricular signal sample point that equals or exceeds a defined R-wave threshold, preferably equal to the programmed ventricular sensitivity.

Figure 7:
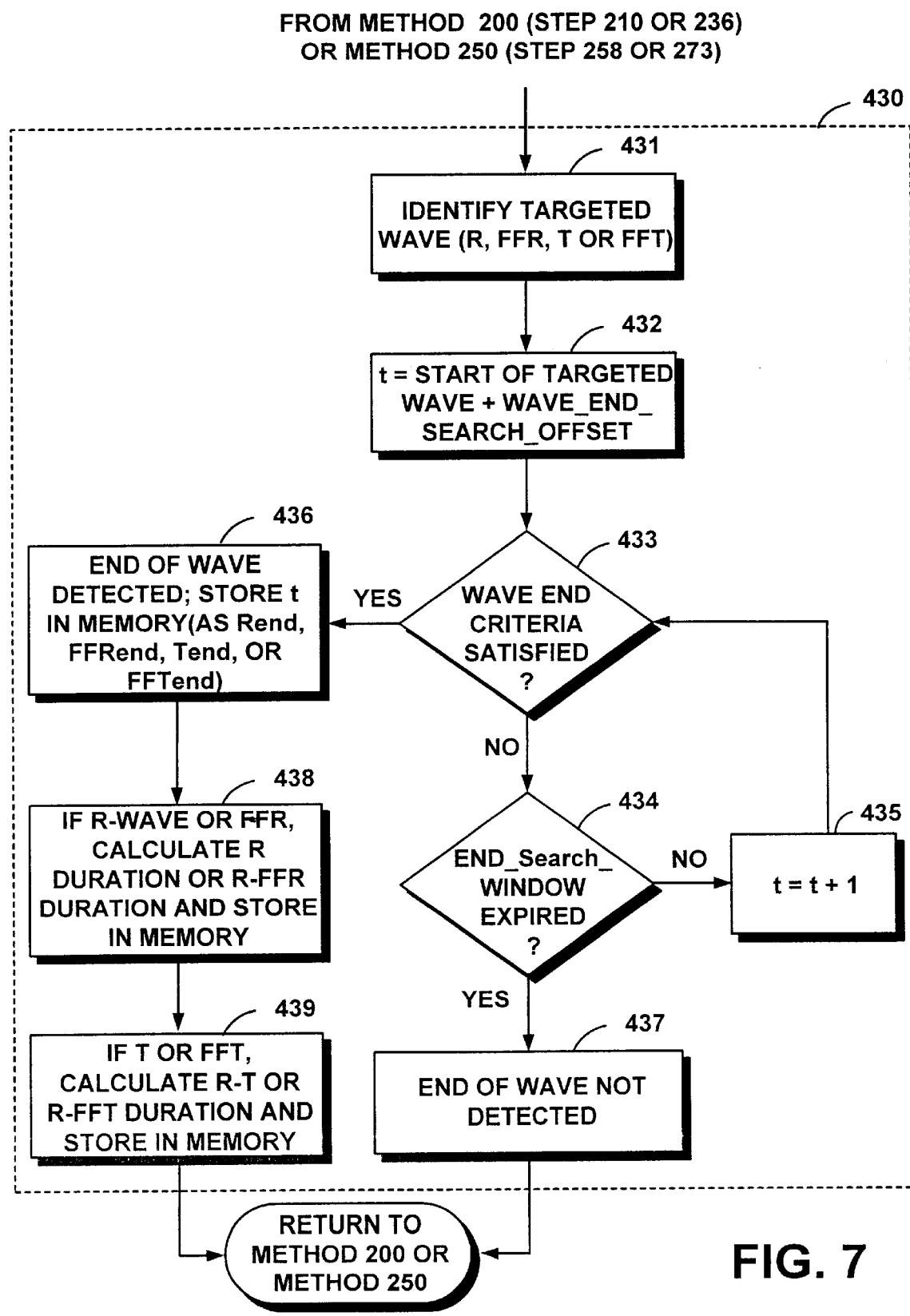
FIG. 7 is a flow diagram that illustrates the details of the methods of operations of FIGS. 3 and 4 for reliably detecting the end of a cardiac event, whether it be the end of the R-wave, the end of the T-wave, the end of the far-field R-wave, or the end of the far-field T-wave.

Method 250 then proceeds to step 258 to search for the end of the R-wave using methods to be further described in conjunction with FIG. 7. At decision step 260, method 250 determines if the end of the R-wave was actually found. The end of the R-wave may not be detected due to noise or because the ventricular sensitivity is too high.

If the end of the R-wave was not detected, method 250 proceeds to decision step 262 to determine if the end of the R-wave has not been detected for a pre-defined number of cardiac cycles, n (e.g. 2 or more consecutive cardiac cycles). If the answer to this inquiry is negative, method 250 returns to step 254 to attempt to detect the end of the R-wave in the next cardiac cycle by repeating steps 256 through 260.

If the answer to the inquiry at decision step 262 is affirmative, that is if the end of the R-wave has not been detected for a given number, n, of consecutive cardiac cycles, then method 250 proceeds to decision step 264 to determine whether the ventricular sensitivity is at the lowest available level. The ventricular sensitivity may be too high at the existing setting to allow for the detection of the end of the R-wave.

Thus, if the ventricular sensitivity is not already at the lowest level available, it is decreased by one programmable setting at step 268. Method 250 then returns to step 254 to attempt to detect the end of the R-wave during the next cardiac cycle at the new, less sensitive, ventricular sensitivity setting. If the ventricular sensitivity is already at its lowest level available as determined at decision step 264, method 250 will be terminated at step 266.

In this way, the ventricular sensitivity is progressively decreased until the end of the R-wave is detected or until the ventricular sensitivity reaches the least sensitive level available. At each ventricular sensitivity setting, a given number, n, of cardiac cycles are searched for the end of the R-wave before the ventricular sensitivity is further decreased. The number n of cardiac cycles searched for the end of the R-wave is preferably a programmable value in the range of 1 to 5.

Figure 6A:
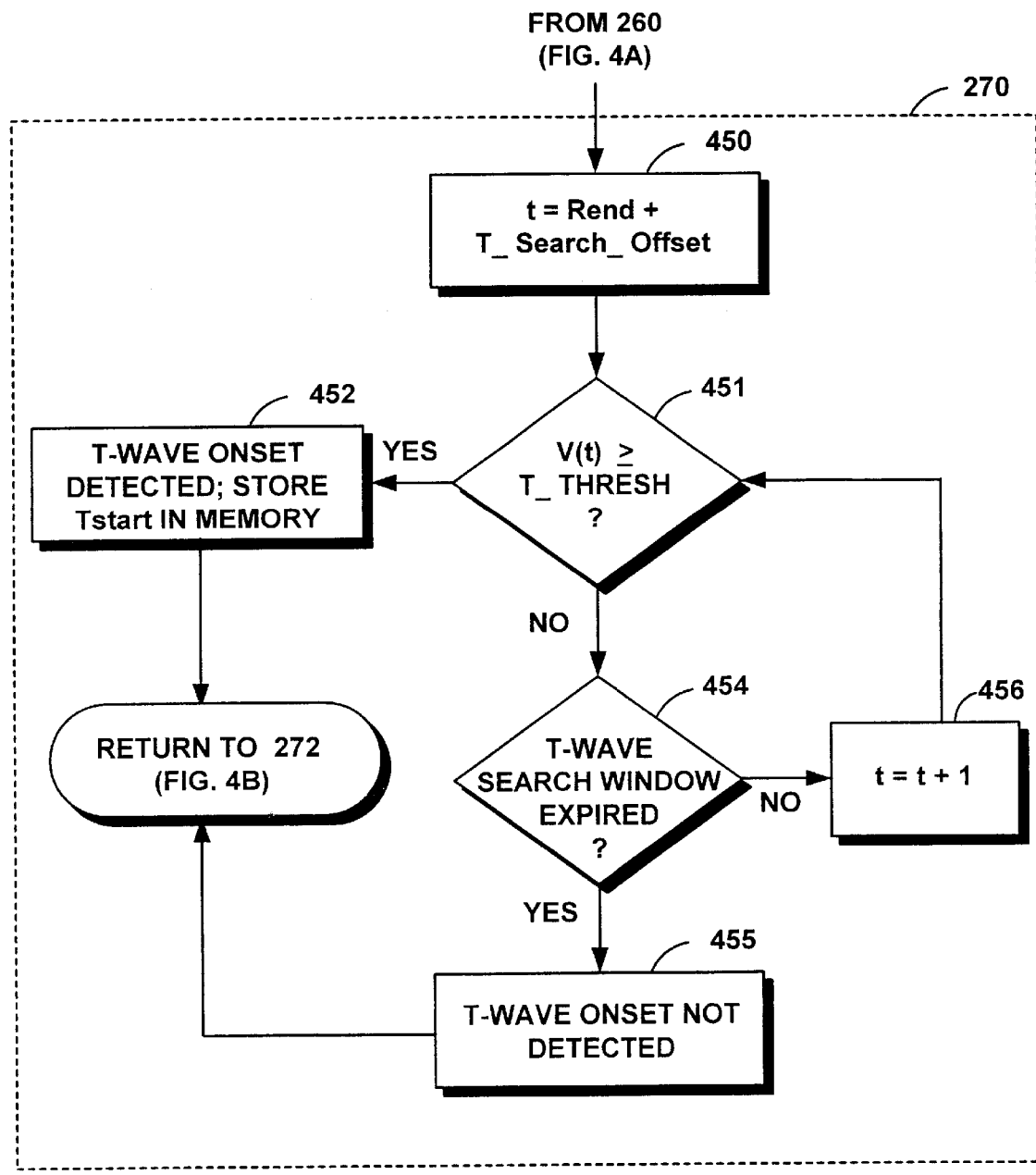
FIG. 6A is a flow diagram that illustrates the details of the methods of operation of FIG. 4 for reliably detecting the onset of the T-waves.

If the end of the R-wave is detected at decision step 260, method 250 proceeds to step 270 to search for the onset of the subsequent T-wave as will described in greater detail in conjunction with FIG. 6A.

Method 250 then proceeds to decision step 272 (FIG. 4B) to determine whether the onset of the T-wave was actually detected. If the onset of the T-wave was not detected, method 250 proceeds to step 274 to determine if the onset of the T-wave has not been detected for a pre-defined number of cardiac cycles, n (e.g., 5 cardiac cycles). If the result of this inquiry is negative, method 250 returns to step 254 (FIG. 4A) to attempt to detect the onset of a T-wave during the next cardiac cycle.

However, if the result of the inquiry at step 274 is affirmative, that is the onset of the T-wave has not been detected during a given number, n, of cardiac cycles, no further attempt is made to detect the onset of the T-wave, and method 250 proceeds to step 276 to check the stability of the measurements related to the R-waves, and to adjust the sensing parameters appropriately as will be described in conjunction with FIG. 9.

Returning to step 272 (FIG. 4B), if the onset of the T-wave has been detected successfully, method 250 proceeds to step 273 to search for the end of the T-wave in a manner to be described in connection with FIG. 7. Method 250 then determines at decision step 278 if the end of the T-wave has been detected successfully. If not, method 250 determines at decision step 280 if the end of the T-wave has not been detected for a pre-defined number of consecutive cardiac cycles, n (e.g., 1 or more). If the result of this inquiry is negative, method 250 returns to step 254 (FIG. 4A) to attempt to detect the end of the T-wave during the next cardiac cycle.

Figure 4A:
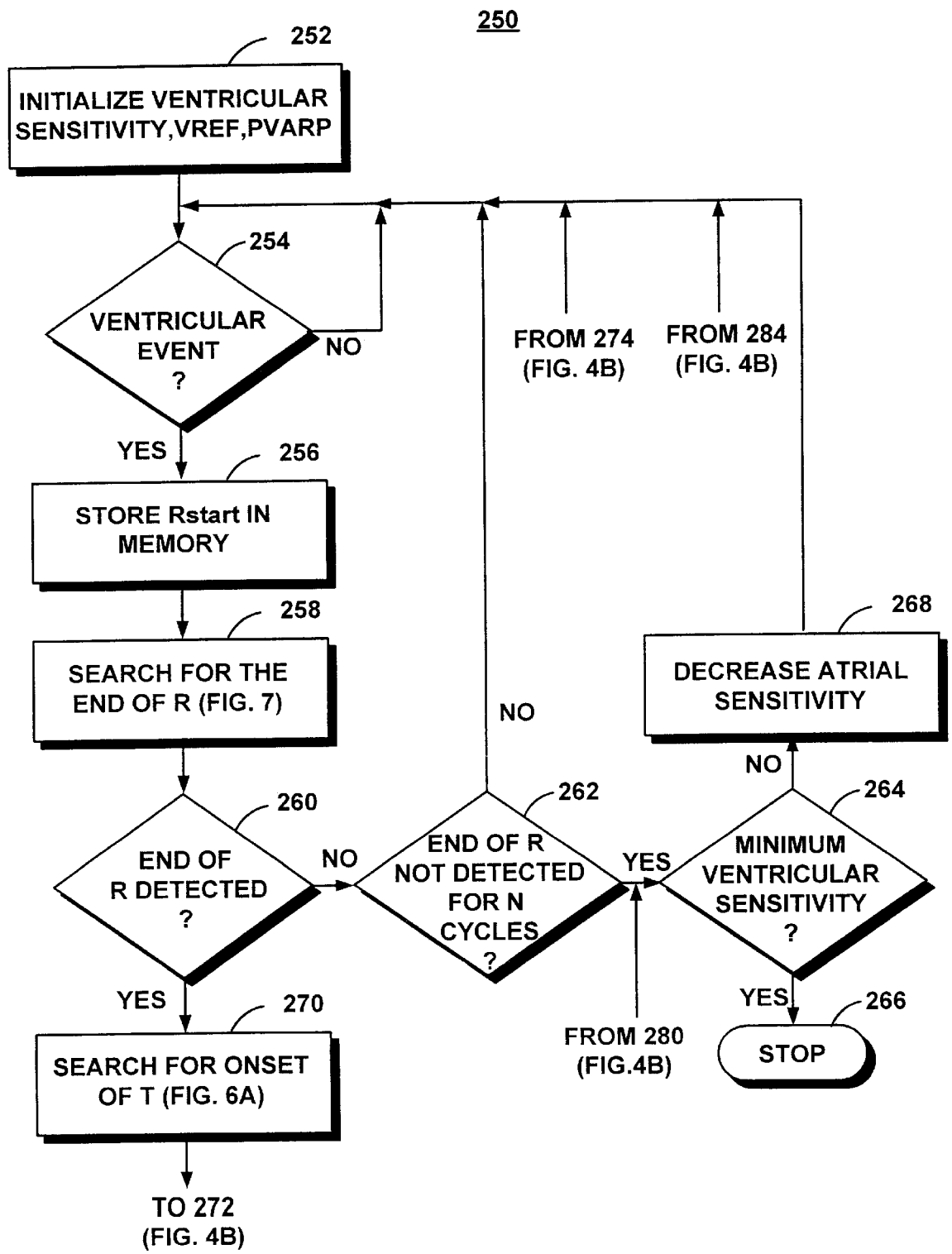
FIG. 4 is comprised of FIGS. 4A and 4B, and represents a flow diagram illustrating an overview of the operation of the stimulation device of FIGS. 1 and 2 in the ventricular channel, for automatically and reliably detecting the onsets and ends of the R-waves and the T-waves, and for adjusting sensing parameters related to the same.
Figure 4B:
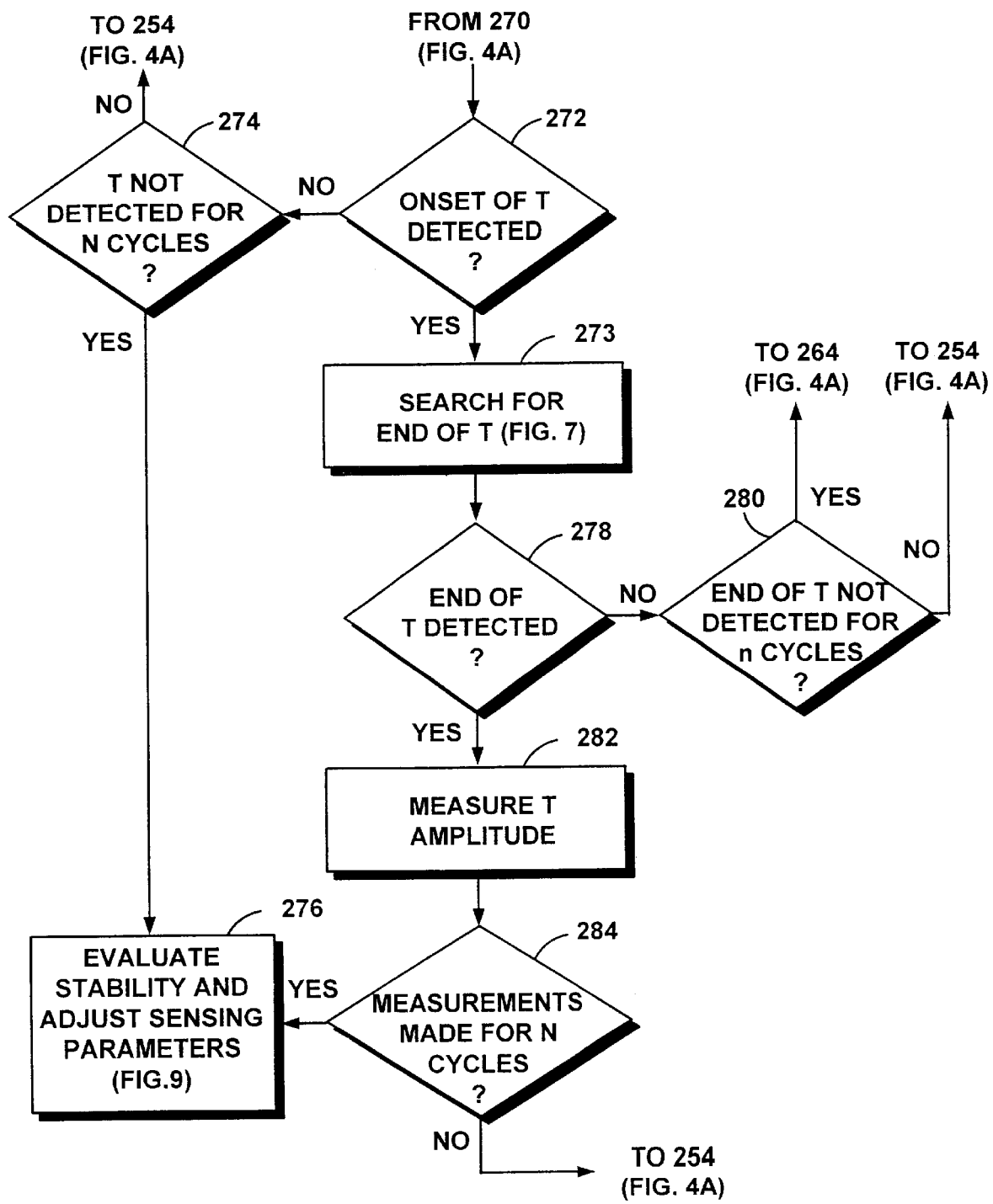

If the result of the inquiry at decision step 280 (FIG. 4B) is affirmative, that is if the end of the T-wave has not been detected for a given number of cardiac cycles, method 250 proceeds to step 264 to determine whether the ventricular sensitivity is at the minimum level available. The end of the T-wave may not have been detected due to noise or because the ventricular sensitivity is too high. Thus, if the ventricular sensitivity is not already at the minimum level available, the ventricular sensitivity is decreased by one programmable setting at step 268. Method 250 then returns to step 254 (FIG. 4A) to attempt to detect the end of the T-wave during the next cardiac cycle at the new, less sensitive, ventricular sensitivity setting. If the ventricular sensitivity is already at its lowest level available, as determined at decision step 264 (FIG. 4A), method 250 will be terminated at step 266 (FIG. 4A).

In this way, the ventricular sensitivity is progressively decreased until the end of the T-wave is detected or until the ventricular sensitivity reaches a minimum setting. At each ventricular sensitivity setting, n cardiac cycles are searched for the end of the T-wave. The number n of cardiac cycles searched for the end of the T-wave is preferably a programmable value, ranging from 1 to 5, and may or may not be equal to the number of cardiac cycles searched for the end of the R-wave.

If the end of the T-wave has been detected as determined at decision step 278 (FIG. 4B), then the maximum ventricular signal amplitude between the detected onset of the T-wave and the detected end of the T-wave is measured and stored in memory 94 as the T-wave amplitude at step 282.

Method 250 then proceeds to step 284 wherein it determines if measurements of the onset and end of the R-waves and T-waves have been made for a desired number of cardiac cycles, N (e.g., 5 cardiac cycles). This number N of cardiac cycles represents the desired number of measurements to be made in order to perform statistical analyses on the measured variables as will be done in the next step 276.

Results from the statistical analyses are used to verify measurement stability and in performing the automatic adjustments of sensing parameters as will be described in conjunction with FIG. 9. The number N of measurements required of each variable is preferably a programmable value ranging from 1 to 10, more preferably 5.

If the desired number, N, of measurements has not yet been made, method 250 is repeated, by returning to step 254 (FIG. 4A), until the desired number of measurements of the onset and end of R-waves, and the onset, end and amplitude of T-waves have been made and stored in memory 94. Once the desired number of measurements have been collected, as determined at decision step 284, method 250 proceeds to step 276 to evaluate the stability of these measurements and adjust sensing parameters related to ventricular sensing (ventricular sensitivity and ventricular refractory) and atrial sensing (post-ventricular atrial refractory period), as will be described in detail in connection with FIG. 9.

The methods by which the present invention detects the onset and end of the far-field R-wave (steps 208 and 220, respectively, in FIG. 3A), the onset and end of the far-field T-wave (steps 232 and 236, respectively, in FIG. 3B), the onset and end of the T-wave (steps 270 and 276, respectively, in FIGS. 4A and 4B, respectively) and the end of the R-wave (step 258, in FIG. 4A), will now be explained in detail in conjunction with FIGS. 5 through 7.

Figure 5:
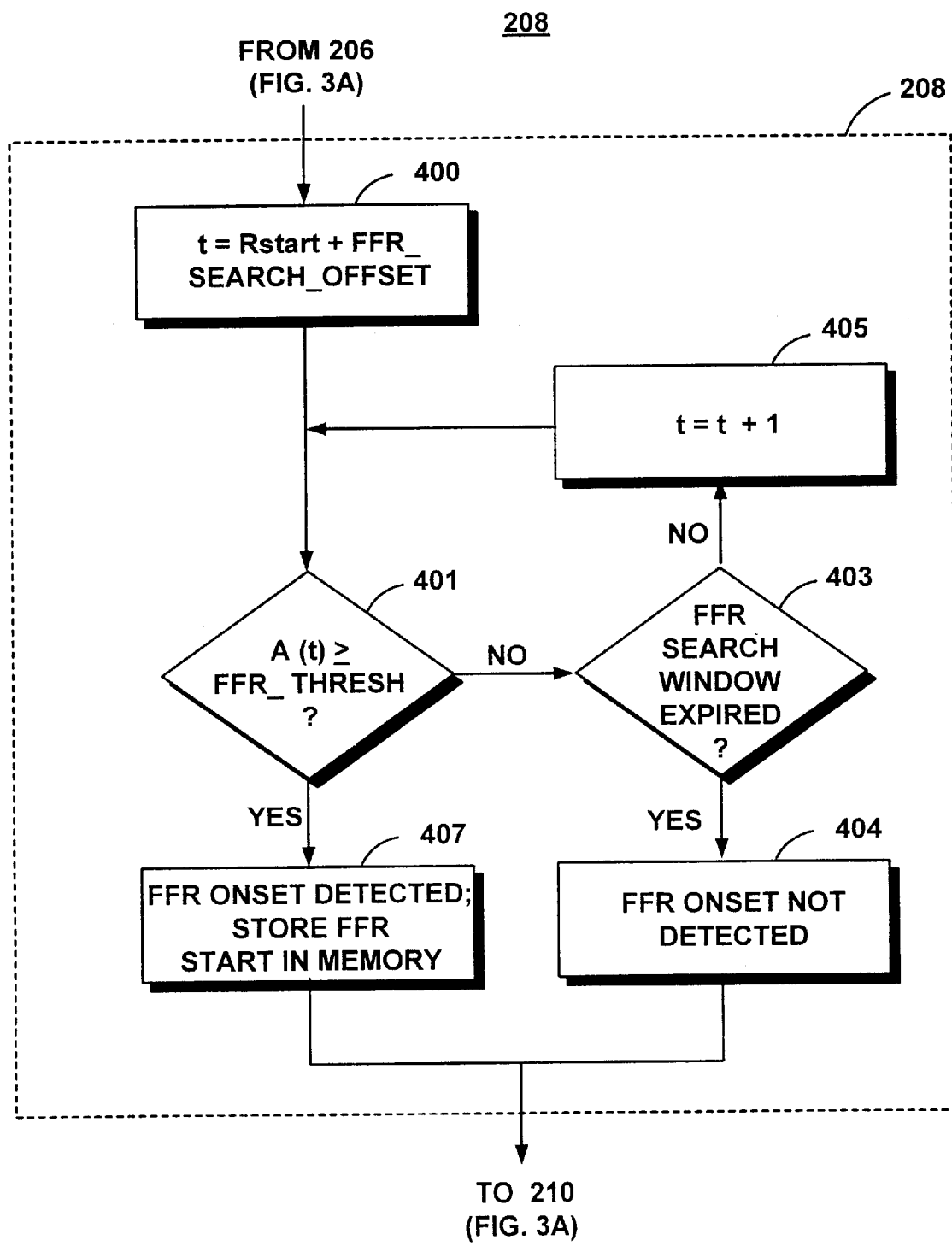
FIG. 5 is a flow diagram that illustrates the details of the methods of operation of FIG. 3 for reliably detecting the onset of the far-field R-waves.

The details of step 208 (FIG. 3A), in which method 200 searches for the onset of the far-field R-wave (FFR), are illustrated in FIG. 5 as a subroutine 208. At step 400, the subroutine 208 starts by initializing the position of a pointer, t, in the memory buffer of A/D converter 90, where the cardiac signals received by atrial sensing circuit 82 and ventricular sensing circuit 84 have been sampled and stored. The pointer, t, is set at the atrial signal sample point occurring at the same time as the start of the R-wave (detected on the ventricular signal and recorded at step 206 of method 200), plus a pre-determined search offset (FFR_search_offset).

This search offset (FFR_search_offset) can be a positive number or a negative number, depending on whether the far-field R-wave is sensed by atrial sensing circuit 82 before or after an R-wave is sensed by ventricular sensing circuit 84. The search offset (FFR_search_offset) is preferably a programmable value (e.g., about 10 ms) and represents the earliest time at which the far-field R-wave is expected to occur in relation to the R-wave.

At step 401, the subroutine 208 determines if the absolute amplitude of the atrial signal sample point, A(t) which pointer t is set at, is greater than a pre-determined far-field R-wave threshold (FFR_thresh). Preferably, the far-field R-wave threshold (FFR_thresh) is equal to the atrial sensitivity, or a predetermined percentage of the atrial sensitivity (e.g., 90%). If, at decision step 401, the amplitude of the atrial signal sample point A(t) is less than the far-field R-wave threshold (FFR_thresh), then the onset of the far-field R-wave has not yet been detected.

The subroutine 208 then determines at decision step 403 whether a far-field R-wave (FFR) search window has expired. The far-field R-wave search window is a pre-defined interval of time (e.g., 50 ms) starting at the initial position of pointer t, as determined at step 400, and extending to the latest time in the cardiac cycle at which a far-field R-wave is expected to occur. If the far-field R-wave search window has expired at step 403, microprocessor 60 is informed, at step 404, that the far-field R-wave (FFR) cannot be detected. The subroutine 208 then returns to the main program module, method 200, proceeding to step 210 in FIG. 3A.

If the far-field R-wave search window has not expired as determined at decision step 403, the pointer, t, is advanced by one time interval at step 405 to the next atrial signal sample point. The next atrial signal sample point A(t) is read from the memory buffer of A/D converter 90 and its amplitude is compared to the far-field R-wave threshold (FFR_thresh) at decision step 401. This process (steps 401 through 405) is repeated until the atrial signal sample point A(t) is found to be greater than or equal to the far-field R-wave threshold (FFR_thresh) or until the far-field R-wave (FFR) search window expires, whichever occurs first.

If the atrial signal sample point A(t) is found to equal or exceed the far-field R-wave threshold (FFR_thresh) at decision step 401, then the subroutine 208 informs microprocessor 60 that the onset of the far-field R-wave has been detected at step 407, and the time at which A(t) first equaled or exceeded the far-field R-wave threshold is stored in memory 94 as the start of the far-field R-wave (FFRstart). The subroutine 208 then returns to the main program module, method 200, proceeding to step 210 in FIG. 3A.

Figure 6B:
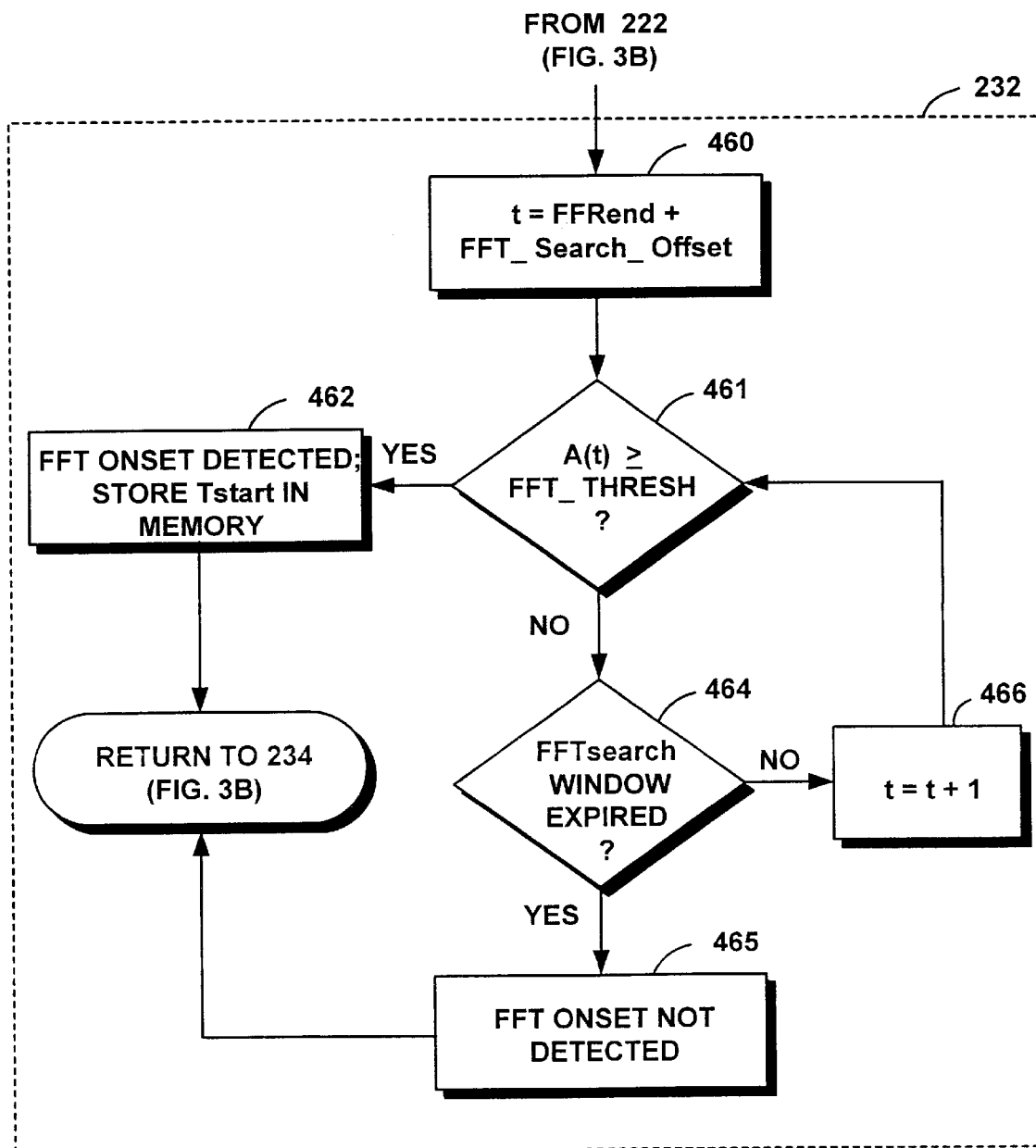
FIG. 6B is a flow diagram that illustrates the details of the methods of operation of FIG. 3 for reliably detecting the onset of the far-field T-waves.

The details of the methods used for searching for the onset of the T-wave (step 270 in FIG. 4A) and the onset of the far-field T-wave (step 232 in FIG. 3B), are illustrated in FIGS. 6A and 6B respectively, as subroutines 270 and 232. The subroutine 270 is called by the method 250 to search for the onset of the T-wave after the method 250 has detected the end of the preceding R-wave (at step 260 of method 250).

With reference to FIG. 6A, subroutine 270 begins at step 450, by moving the position of pointer, t, in the memory buffer of the A/D converter 90, to the ventricular signal sample point V(t) identified as the end of the preceding R-wave (Rend) plus a pre-defined T-wave search offset (T_Search_Offset). This search offset approximates the shortest interval anticipated between the end of the R-wave and the start of the T-wave. It is preferably a programmable value and typically on the order of 50 msec.

At step 451, the amplitude of the ventricular signal sample point V(t) is compared to a predefined threshold for detecting the onset of the T-wave (T_thresh). This T-wave threshold may be a fixed value (e.g., 0.3 mv), or a percentage of the ventricular sensitivity (e.g., 50%) and is preferably programmable. If, at decision step 451, the absolute amplitude of the current sample point V(t) is lower than the T-wave threshold, the subroutine 270 proceeds to step 454 to determine if a T-wave search window has expired. The T-wave search window is a predefined interval of time starting at the initial position of pointer t as determined at step 450 and extending to the latest time in the cardiac cycle at which a T-wave is expected to occur. The duration of the T-wave search window is preferably a programmable value, typically 400 ms.

If the T-wave search window has expired as determined at decision step 454, the subroutine 270 proceeds to step 455 to inform the microprocessor 60 that the onset of the T-wave cannot be detected. If the T-wave search window has not expired at decision step 454, the subroutine 270 proceeds to step 456 and advances the pointer, t, by one time interval, to the next ventricular signal sample point. The next ventricular signal sample point V(t) is read from the memory buffer of A/D converter 90 and its amplitude is compared to the T-wave threshold (T_thresh) at decision step 451.

When the absolute amplitude of the sample point V(t) is greater than or equal to the T-wave threshold (T_thresh) as determined at decision step 451, the subroutine 270 proceeds to step 452 to inform the microprocessor 60 that the onset of the T-wave has been detected, and the time at which V(t) first equaled or exceeded the T-wave threshold is stored in memory 94 as the start of the T-wave (Tstart). The subroutine 270 then returns to the main program module, the method 250, proceeding to step 272 in FIG. 4B.

FIG. 6B depicts a subroutine 232 that is called upon by method 200 of FIG. 3, for searching for the onset of a far-field T-wave after the end of a preceding far-field R-wave has been detected (at step 222 of method 200). Subroutine 232 begins at step 460, by moving the pointer, t, in the memory buffer of A/D converter 90, to the atrial signal sample point A(t) defined by the time at which the end of the preceding far-field R-wave (FFRend) was detected plus a pre-defined far-field T-wave search offset (FFT_Search_Offset). This search offset approximates the shortest interval anticipated between the end of the preceding far-field R-wave and the start of the far-field T-wave. It is preferably a programmable value, typically about 50 msec.

At step 461, the amplitude of the atrial signal sample point A(t) is compared to a pre-defined threshold for detecting the onset of the far-field T-wave (FFT_thresh). This far-field T-wave threshold may be a fixed value (e.g., 0.3 mv), or a percentage of the atrial sensitivity (e.g., 50%) and is preferably programmable. If, at decision step 461, the absolute amplitude of the current sample point A(t) is less than the far-field T-wave threshold, the subroutine 232 proceeds to step 464 to determine if a far-field T-wave (FFT) search window has expired. The far-field T-wave search window is a pre-defined interval of time starting at the initial position of pointer t as determined at step 460 and extending to the latest time in the cardiac cycle at which a far-field T-wave is expected to occur. The duration of the far-field T-wave search window is preferably a programmable value, typically about 400 ms.

If the far-field T-wave search window has expired as determined at decision step 464, the subroutine 232 proceeds to step 465 to inform the microprocessor 60 that the far-field T-wave cannot be detected. If the far-field T-wave search window has not expired at decision step 464, the subroutine 232 proceeds to step 466 and advances the pointer, t, by one time interval, to the next atrial signal sample point. The next atrial signal sample point A(t) is read from the memory buffer of A/D converter 90 and its amplitude is compared to the far-field T-wave threshold (FFT_thresh) at decision step 461.

When the absolute amplitude of the atrial signal sample point A(t) is greater than or equal to the far-field T-wave threshold (FFT_thresh) as determined at decision step 461, the subroutine 232 proceeds to step 462 to inform the microprocessor 60 that the onset of the far-field T-wave has been detected, and the time at which A(t) first equaled or exceeded the far-field T-wave threshold is stored in memory 94 as the start of the far-field T-wave (FFTstart). The subroutine 232 then returns to the main program module, method 200, proceeding to step 234 in FIG. 3B.

The details for searching for the end of the R-wave, the end of the far-field R-wave, the end of the T-wave and the end of the far-field T-wave (steps 220, 236, 258 and 276, respectively, of FIGS. 3 and 4) are illustrated in FIG. 7 as a subroutine 430. At step 431, subroutine 430 starts by determining which wave, R-wave, far-field R-wave, T-wave or far-field T-wave, is being analyzed. Different sets of parameters may be used by subroutine 430 in searching for the end of each of these different events. Thus, the appropriate set of parameters must be loaded at step 431 according to which wave is being analyzed.

When subroutine 430 is called upon, by either method 200 or method 250, pointer t will initially be positioned at the atrial or ventricular signal sample point detected as the onset of the wave being analyzed (i.e., the start of the R-wave, the start of the T-wave, the start of the far-field R-wave or the start of the far-field T-wave). Therefore, at step 432, the subroutine 430 advances the pointer t by a predefined time interval from its initial position to a new signal sample point (atrial or ventricular depending on the wave being analyzed) stored in the memory buffer of A/D converter 90.

This predefined interval by which pointer t is advanced represents the earliest time at which the end of the targeted wave is expected to occur and is referred to as the Wave_End_Search_Offset. For the R-wave and the far-field R-wave, the Wave_End_Search_Offset is preferably about 20 ms and represents the shortest expected duration of the R-wave. For the T-wave and the far-field T-wave, the Wave_End_Search_Offset is preferably about 5 ms and represents the shortest expected duration of the T-wave.

At step 433, the subroutine 430 evaluates the sampled signal to determine if the end of the wave has occurred as defined by a given set of criteria. For successful detection of the end of the wave, the following two criteria must be met:

$$(1) \quad \left| \sum_{i=0}^{i=a} S(t+i) - S(t+i+\Delta t) \right| < \text{End\_Threshold}$$

$$\text{maximum of } |S(t:t+a+\Delta t)| < \text{Max\_End\_Amplitude} \quad (2)$$

Criteria (1) requires that the absolute value of the summation of the differences between a given number of consecutive pairs of sample points occurring Δt msec apart is less than a pre-defined value, End_Threshold. In Criteria (1), "t" is the time of the initial signal sample S(t) which may represent the atrial signal A(t) or the ventricular signal V(t) depending on the wave being analyzed; "a" is the number of signal sample pairs to be included in the calculation of criteria (1); and Δt is the time interval between a pair of sample points. The values for "a" and "Δt" are pre-defined constants, which may be the same or different when searching for the end of the R-wave, the end of the far-field R-wave, the end of the T-wave or the end of the FFT. Preferably, "a" is 5 samples (or 10 ms when sampling rate is 500 Hz); and Δt is 5 samples (or 10 ms when sampling rate is 500 Hz).

Thus, in the present example, the difference in amplitude between the signal sample point occurring at time t and a sample point occurring Δt (10 msec) later is summed with the differences in amplitudes between the next a samples (5 samples) consecutively following S(t) and the corresponding sample points occurring Δt later. This summation must be less than End_Threshold. The value of End_Threshold can be fixed (e.g., 0.2 mV), or it can be a percentage of the ventricular or atrial sensitivity depending which signal is being analyzed (e.g., 18% of the sensitivity).

Criteria (1) is based on the fact that as the targeted wave ends, the difference in amplitude between consecutively sampled points will diminish. Thus, by comparing the change in amplitude between sample points to some maximum allowed change, the end of the targeted wave can be detected.

Criteria (2) requires that the maximum amplitude of all the signal sample points used in satisfying Criteria (1) must be less than a pre-defined maximum amplitude (Max_End_Amplitude). In other words, the amplitude of the first point S(ti) and the amplitude of the last point S(t+a+Δt) of Criteria (1) and all sample points in between must be less than an allowable maximum amplitude (Max_End_Amplitude). This maximum amplitude may be defined differently for each wave being analyzed and may be a fixed value approximating the noise amplitude (e.g., 0.2 mV), or it may be a percentage of the atrial or ventricular sensitivity (e.g., 50%) depending on which wave is being analyzed.

If either criteria (1) or (2) is not met, indicating that the end of the targeted wave has not yet been detected, the subroutine 430 proceeds to step 434, to determine whether a predefined search window (End_search_window) has expired. This search window begins at the starting pointer t position as defined at step 432 and extends for the maximum duration expected for the targeted wave. The duration of the end search window is preferably a programmable value and may be different for the R-wave, the far-field R-wave, the T-wave and the far-field T-wave. For example, the search window for detecting the end of the R-wave or the end of the far-field R-wave may be 200 msec long; the search window for detecting the end of the T-wave or the end of the far-field T-wave may be 300 msec long.

If this end search window has not expired as determined at decision step 434, subroutine 430 proceeds to step 435, where the pointer t is advanced one time interval to the next sampled point of the atrial or ventricular signal, depending on which wave is being analyzed. Subroutine 430 then returns to step 433 to evaluate the next set of sampled points in terms of criteria (1) and (2) as described above, beginning at the new sample point S(t). If the end search window expires as determined at decision step 434 before criteria (1) and (2) are satisfied, the microprocessor 60 is informed that the end of the targeted wave cannot be detected at step 437. Subroutine 430 returns to the appropriate step of the main program module, method 200 or 250, whichever originated subroutine 430.

If both criteria (1) and (2) are found to be satisfied at decision step 433, the end of the targeted wave is considered detected. The microprocessor 60 is notified of the wave-end detection at step 436, and the current position of pointer, t, is saved in memory 94 as the time at which the targeted wave ends, either the end of the R-wave (Rend), end of the far-field R-wave (FFRend), end of the T-wave (Tend) or end of the far-field T-wave (FFTend). If the targeted wave is an R-wave or a far-field R-wave, the duration of the R-wave (R duration) and the duration from the start of the R-wave to the end of the far-field R-wave (R-FFR duration) are calculated and stored in memory 94 at step 438. The R-wave duration and the R-FFR duration are determined by measuring the time from the start of the R-wave (as detected at step 206, FIG. 3A) to the end of the R-wave or the end far-field R-wave, respectively, as determined at step 436.

If the targeted wave is a T-wave, then at step 439, the duration of the R-T segment of the cardiac cycle (R-T duration) is determined by measuring the time from the start of the R-wave (as determined at step 256, FIG. 4A) to the end of T-wave as determined at step 436. Likewise, if the targeted wave is a far-field T-wave, the duration of the R-FFT segment of the cardiac cycle is determined by measuring the time from the start of the R-wave as determined at step 206 (FIG. 3A) to the end of the far-field T-wave as determined at step 436. The start of the R-wave is the time at which a ventricular intrinsic event is sensed at step 204 in FIG. 3. The R-T duration and the FFR-FFT duration are stored in memory 94 at step 439.

The subroutine 430 is thus complete and returns to the main program module, either method 200 (FIG. 3) or method 250 (FIG. 4), whichever method called upon subroutine 430 initially, and proceeds to the next step (to step 222 if the far-field R-wave has been analyzed or step 238 if the far-field T-wave has been analyzed in method 200; to step 260 if the R-wave has been analyzed or step 278 if the T-wave has been analyzed in method 250).

Figure 8B:
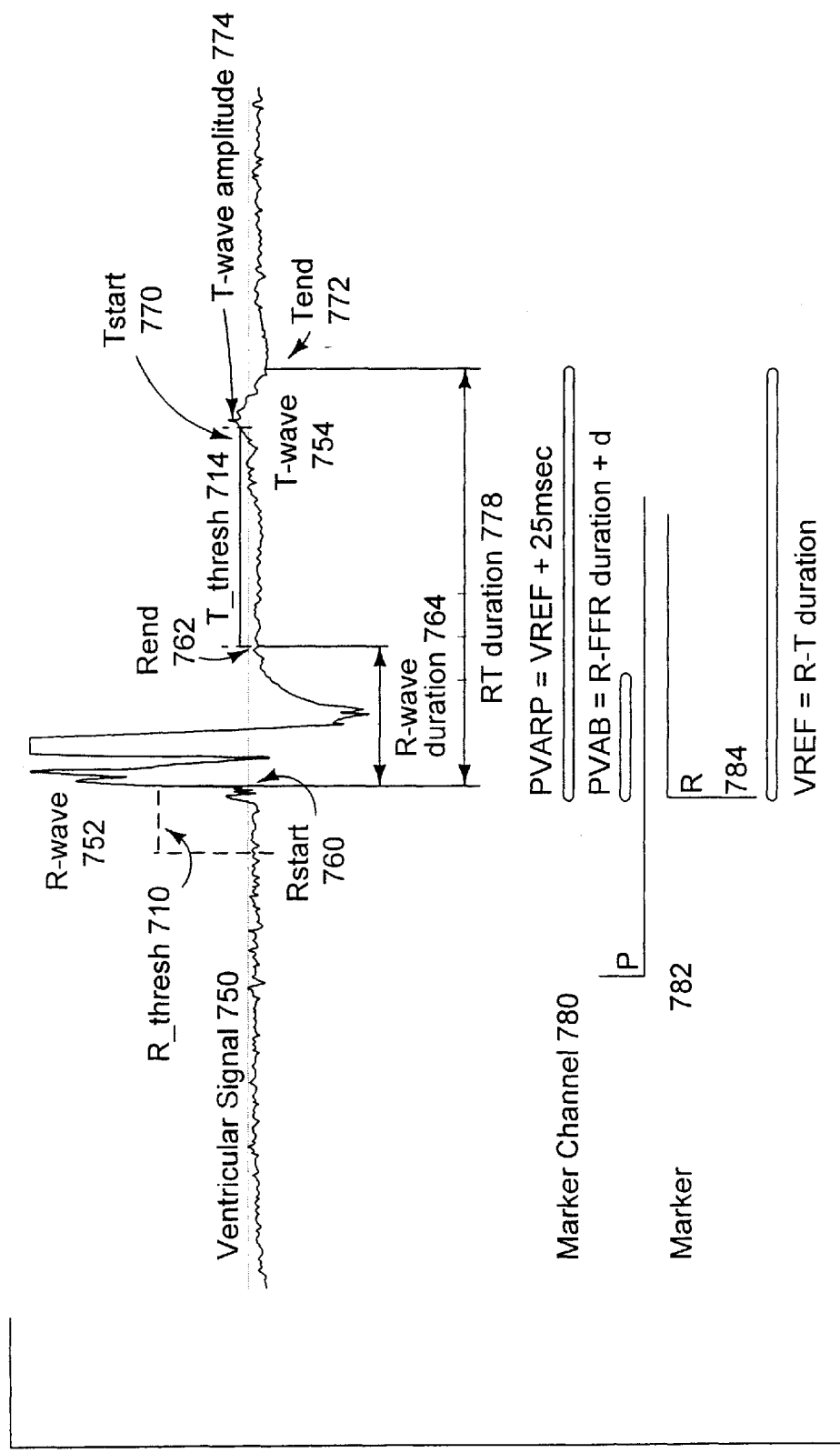
FIG. 8 is comprised of FIGS. 8A and 8B, and illustrates sample recordings of atrial and ventricular cardiac signals in which some of the measured variables are determined by the methods of operations of FIGS. 3 and 4.

FIG. 8 is comprised of FIGS. 8A and 8B, and illustrates exemplary recordings of: a surface ECG signal 700; an atrial signal 725 as sensed by the atrial sensing circuit 82; and a ventricular signal 750 (FIG. 8B) as sensed by ventricular sensing circuit 84. P-wave 702, R-wave 704, and T-wave 706 are indicated on the surface ECG signal 700. The corresponding P-wave 727 sensed on the atrial signal 725 and the corresponding R-wave 752 and T-wave 754 sensed on the ventricular signal 750 are also indicated. A marker channel signal 780 is shown as the bottom trace of FIG. 8. A marker signal labeled 'P' 782 indicates the detection by device 10 of a P-wave. A marker signal labeled 'R' 784 indicates the detection of an R-wave by the stimulation device 10.

On the atrial signal 725, a far-field signal 729 occurring just subsequent to the R-wave 752 of the ventricular signal 750 is easily observable. This far-field signal 729 is referred to as the far-field R-wave (FFR). According to method 200 described above, the atrial signal 725 will be processed to detect the onset of the far-field R-wave (FFRstart) 730, and the end of the far-field R-wave (FFRend) 732, so that the total duration of the R-wave and far-field R-wave (R-FFR duration) 734 can be measured.

The onset of the far-field R-wave (FFRstart) 730 is detected as time at which the atrial signal 725 first equals or exceeds a pre-defined far-field R-wave threshold (FFR_thresh) 710. The end of the far-field R-wave (FFRend) 732 is found as described previously in conjunction with the subroutine 430 shown in FIG. 7 in which a diminished difference between the amplitudes of consecutively sampled points from atrial signal 725 is detected. In this example recording, a far-field T-wave signal associated with the T-wave 754 occurring on the ventricular signal 750 is not observable on the atrial signal 725.

According to the method 250 described above, the ventricular signal 750 will be processed to detect the onset of the R-wave (Rstart) 760 and the end of the R-wave (Rend) 762 in order to measure the R-wave duration 764. Further, method 250 processes the ventricular signal 750 to detect the onset of the T-wave (Tstart) 770 and the end of the T-wave (Tend) 772 so that the T-wave amplitude (774) can be measured. In addition, the duration of the R-T segment (RT duration) 778 of the ventricular signal 750 can be measured by knowing the time of the onset of the R-wave (Rstart) 760 and the end of the T-wave (Tend) 772. The onset of the R-wave (Rstart) 760 is detected as the time at which the ventricular signal 750 first equals or exceeds an R-wave threshold (R_thresh) 710. Likewise, the onset of the T-wave (Tstart) 770 is detected as the time at which the ventricular signal 750 first equals or exceeds a T-wave threshold (T_thresh) 714 as has been described in conjunction with FIG. 6A. The end of the R-wave (Rend) 762 and the end of the T-wave (Tend) 772 are found as described previously in conjunction with the subroutine 430 shown in FIG. 7 in which a diminished difference between the amplitudes of consecutively sampled points from ventricular signal 750 is detected.

The measurements indicated in FIG. 8 are made over a desired number of cardiac cycles such that average values for these measurements can be obtained and used in automatically adjusting sensing parameters as will be described in conjunction with FIG. 9. For example, by detecting the amplitude of the far-field T-wave (not shown), the atrial sensitivity can be advantageously adjusted to be greater than the average far-field T-wave amplitude to prevent oversensing of far-field T-waves by atrial sensing circuit 82.

By measuring the total duration of the R-wave and far-field R-wave (R-FFR duration) 734, the post-ventricular atrial blanking period (PVAB) can be set to extend through the end of the far-field R-wave (FFR) 729 such far-field R-waves are not detected and mistakenly identified as P-waves by device 10. The post-ventricular atrial blanking period (PVAB) is initiated by the microprocessor 60 in the atrial channel whenever an R-wave (752) is detected by the ventricular sensing circuit 84. Therefore, setting the post-ventricular atrial blanking period (PVAB) to be equal to or greater than the total duration of the R-wave and far-field R-wave (R-FFR duration) 734 ensures that blanking of the atrial sensing circuit 82 throughout the far-field R-wave prevents mis-detection of far-field R-waves as P-waves. In this way, reliable detection of P-waves in the atrial channel and accurate detection of the atrial rate by device 10 is ensured.

Oversensing of T-waves in the ventricular channel can be prevented by measuring the T-wave amplitude 774 of the ventricular signal 750 and adjusting the ventricular sensitivity to be greater than the average T-wave amplitude. By measuring the duration of the total R-T segment (R-T duration) 778 of the ventricular signal 750, the ventricular refractory period can be set to extend through the end of the T-wave such that if sensing does occur during this period, any event is detected as a refractory-sensed event and is not detected as an R-wave. In this way, reliable sensing of R-waves in the ventricular channel and accurate detection of the ventricular rate by device 10 is ensured.

Furthermore, the post-ventricular atrial refractory period (PVARP) can be set in the atrial channel based on the measurement of the R-T duration 778. By setting the post-ventricular atrial refractory period (PVARP) slightly longer than the average R-T duration 778, far-field T-waves sensed during the post-ventricular atrial refractory period (PVARP) are detected by the atrial channel as refractory-sensed events are not used in determining atrial rate by device 10.

The details by which methods 200 and 250 automatically adjust the sensing parameters based on the measurements just described will now be provided in conjunction with FIG. 9. At step 246 (FIG. 3B) and step 276 (FIG. 4B), methods 200 and 250, respectively, call upon a subroutine 500 to verify the stability of the measurements made during the processing of the atrial signal (method 200) and/or the ventricular signal (method 250) and to automatically adjust the sensing parameters as appropriate. In practice steps 244 and 276 could exist as separate subroutines, however, they are herein described as one subroutine 500 for the sake of convenience.

Figure 9A:
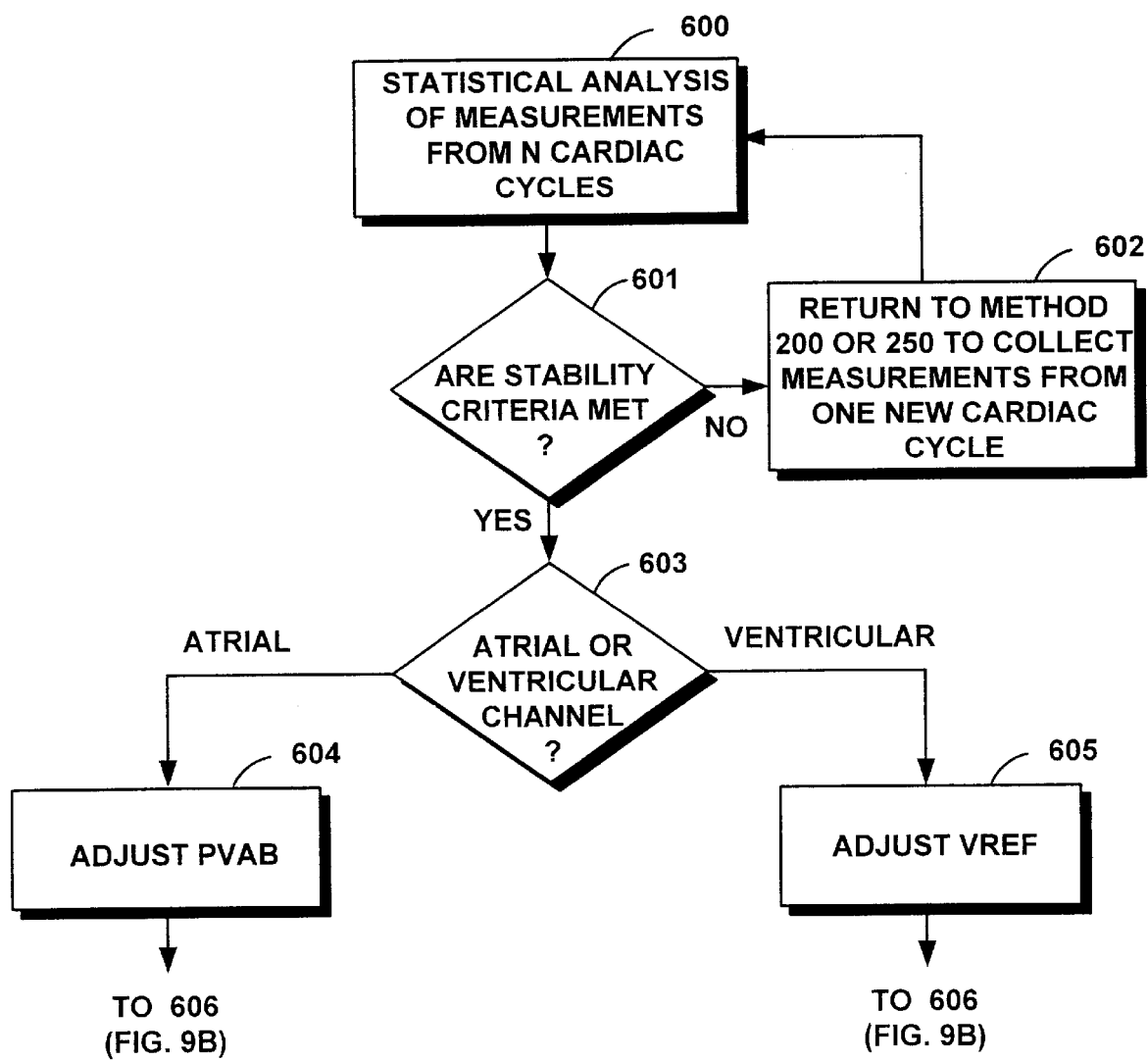
FIG. 9 is comprised of FIGS. 9A and 9B, and represents a flow diagram that illustrates the details of the methods of operations of FIGS. 3 and 4 for automatically adjusting sensing parameters based on the measurements of variables associated with the detection of the onsets and ends of R-waves, T-waves, far-field R-waves and far-field T-waves.
Figure 9B:
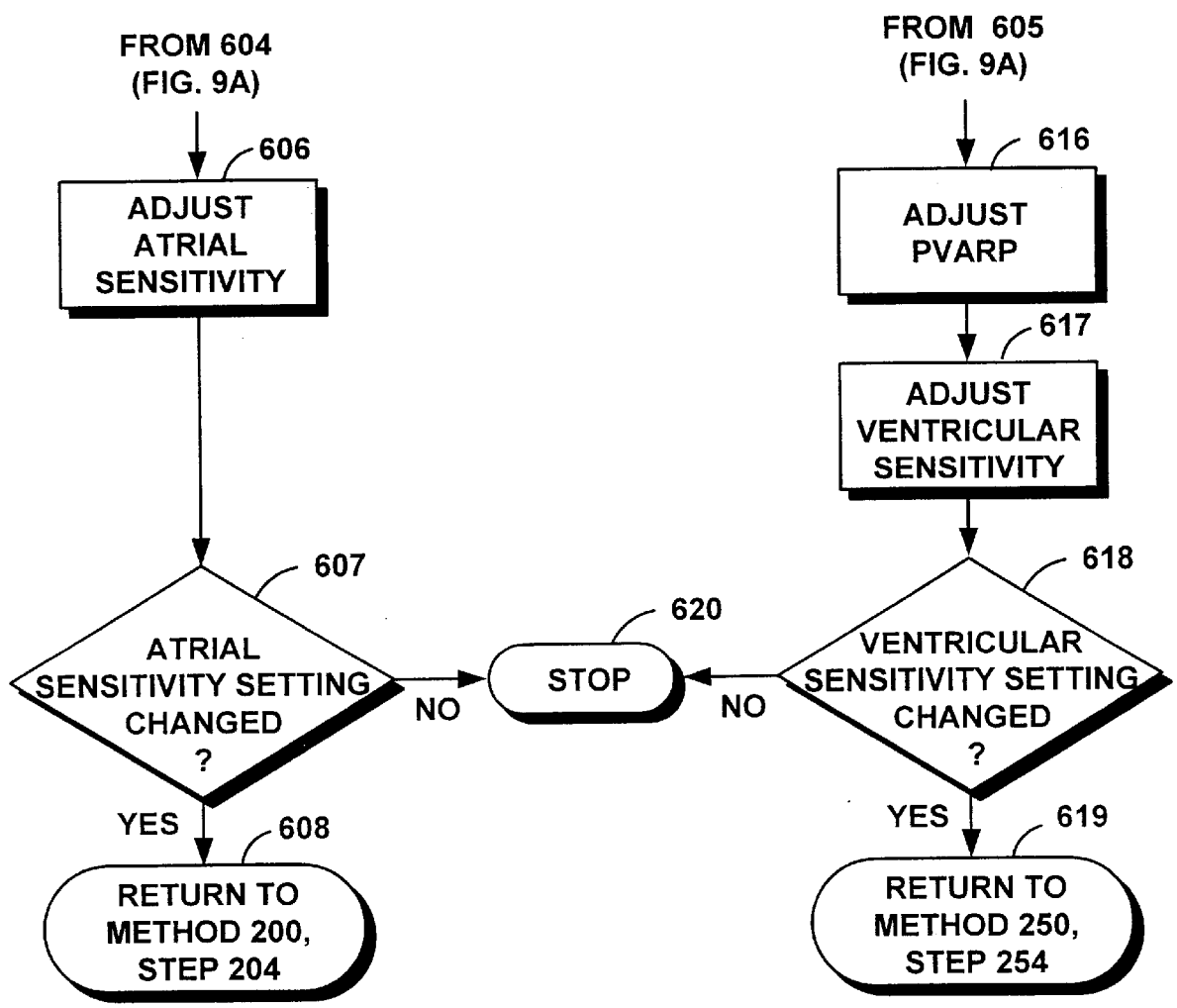

In FIG. 9 (FIGS. 9A and 9B), subroutine 500 starts at step 600, where a statistical analysis of the measurements made in methods 200 and 250 is performed. Preferably, at least the means and standard deviation of the R-wave duration and the far-field R-wave duration are calculated. If methods 200 and/or 250 were also successful in detecting the onset and end of the far-field T-waves (FFT) or the T-waves, the means and the standard deviations of the R-T duration or the FFR-FFT duration, the T-wave amplitude or the far-field T-wave amplitude are also calculated at step 600.

Method 500 proceeds to step 601 to evaluate the statistical results according to predefined stability criteria. Specifically, the standard deviation of the measurements calculated at step 600 should be less than some maximum standard deviation. This maximum standard deviation is preferably a programmable value equal to a percentage of the mean. For example, in one embodiment, the following criteria must be met to verify stability of the measurements:

(1) R_Duration_Variation<R_Duration_Mean/8; and (if the T-wave or the far-field T-wave are detectable)

(2) R-T_Duration_Variation<R-T_Duration_Mean/4; and (3) T-Wave_Amplitude_Variation<T_Wave_Amplitude_Mean/4.

According to criteria (1), the standard deviation of the R-wave duration (R_Duration_Variation) must be less than one-eighth of the mean R-wave duration (R_Duration_Mean). According to criteria (2), the standard deviation of the R-T duration (R-T_Duration_Variation) must be less than one-fourth of the mean R-T duration (R-T_Duration_Mean). According to criteria (3), the standard deviation of the T wave amplitude (T_Wave_Amplitude_Variation) must be less than one-fourth of the mean T wave amplitude (T_Wave_Amplitude_Mean).

In other embodiments, other statistical or mathematical analyses or differently defined stability criteria could be used to verify that the cardiac signals were stable during the measurements of methods 200 and 250 (e.g., the mean or peak heart rates not exceeding a given maximum, the standard deviation of the R-wave amplitude less than 1 millivolt, the mean or peak activity level as determined by the physiologic sensor 108 less than a given maximum, etc.). Regardless of the analyses or criteria used, it is the intention in the subroutine 500 to verify that the cardiac signals were stable during the operation of the methods 200 and/or 250 before making any automatic adjustments to the sensing parameters based on the measurements made by the methods 200 and 250. In this way, adjustments to sensing parameters are not made based on anomalous data.

If any of the stability criteria are not met at step 601, then the cardiac signals during the data acquisition of methods 200 and 250 are considered unstable, possibly due to unstable cardiac function or due to noise. Thus, the measurements of methods 200 and/or 250 are not deemed reliable and are not used by method 500 to automatically adjust the sensing parameters at this time. Instead, method 500 proceeds to step 602 to collect another set of measurements during the next cardiac cycle by returning to the main program module, method 200 or method 250, whichever called upon subroutine 500. Once a one new set of measurements has been collected from one additional cardiac cycle, the oldest set of measurements is discarded and replaced by the new set of measurements in memory 94. The subroutine 500 then returns to step 600 and the new measurements are used in the statistical analysis made at step 600.

If the stability criteria are all met at decision step 601, the cardiac signals acquired during the operation of the methods 200 or 250 are considered stable and the measurements made of the onsets and ends of cardiac events deemed reliable. Subroutine 500 then proceeds to step 603 to begin to adjust the sensing parameters.

At decision step 603, subroutine 500 determines which signal, atrial or ventricular, is being analyzed. This is known by determining which main program module, method 200 or method 250, has called upon the subroutine 500. If the method 200 has called upon the subroutine 500, the atrial signal is being analyzed and the subroutine 500 will proceed to step 604 to adjust atrial sensing parameters.

At step 604, post-ventricular atrial blanking (PVAB) is automatically adjusted as a function of the far-field R-wave (FFR) duration. Preferably, PVAB is set equal to the mean far-field R-wave duration (FFR_Duration_Mean) calculated at step 600 plus some predefined safety margin, $\Delta A$:.

$$PVAB = FFR\_Duration\_Mean + \Delta$$

where the safety margin, $\Delta$, may be programmed to be zero or some other constant, for example 25 msec, or it may be programmed as a variable such as the standard deviation of the far-field R-wave duration. At step 606, the atrial sensitivity is adjusted in relation to the mean far-field T-wave amplitude determined at step 600. In the preferred embodiment, the atrial sensitivity will be:

(1) increased by one programmable setting if the mean far-field T-wave amplitude is less than 40% of the current atrial sensitivity setting, (2) decreased by one programmable setting if the mean far-field T-wave amplitude is greater than 80% of the current atrial sensitivity setting, or (3) unchanged if the mean far-field T-wave amplitude is between 40% and 80% of the current atrial sensitivity setting.

Furthermore, the atrial sensitivity is only increased or decreased if it remains within a pre-defined range bounded by a maximum and minimum setting. If the far-field T-wave was not detected by method 200 such that the calculation of the mean far-field T-wave amplitude cannot be made, the atrial sensitivity is set to a default setting, for example 0.5 millivolt, or it may remain unchanged from the last setting in effect prior to the initiation of method 200.

At decision step 607, subroutine 500 determines if an adjustment to the atrial sensitivity has been made. If so, subroutine 500 returns to step 204 of method 200 (step 608) to collect data for another "N" cardiac cycles, where N is the desired number of measurements to be collected and stored in memory 94 each time method 200 is enabled, before stability is verified and sensing parameters are adjusted. In this way, the method 200 is continuously repeated until the atrial sensitivity needs no further adjustment.

Once the atrial sensitivity no longer needs adjusting, either because it is already at the highest or lowest level allowed or because it does not need to be changed according to criteria (3) above, the subroutine 500 will be terminated at step 620. Method 200 has thus completed the automatic adjustment of the atrial sensing parameters and these parameters will remain unchanged until the next time method 200 is enabled by the microprocessor 60.

If the subroutine 500 has been called by the method 250 as determined at decision step 603, then sensing parameters related to the ventricular channel (ventricular sensitivity and ventricular refractory) as well as post-ventricular atrial refractory period (PVARP) will be adjusted. At step 605, the ventricular refractory period (VREF) is adjusted in relation to the mean R-T duration determined at step 600. In one embodiment, the ventricular refractory period (VREF) is set equal to the mean R-T duration, but preferably not longer than some pre-defined maximum, for example 275 msec. If the T-wave was not detected by method 250 such that the R-T duration could not be measured, the ventricular refractory period (VREF) will be set equal to a nominal value (e.g., 250 ms) stored in memory 94, or it may remain unchanged from the last setting in effect prior to the initiation of method 250.

At step 616, the post-ventricular atrial refractory period (PVARP) is adjusted as a function of the R-T duration or, equivalently, a function of the ventricular refractory period (VREF). In the preferred embodiment, $$PVARP=VREF+25 \text{ ms.}$$

Alternatively, if the onset and end of the far-field T-wave were detected during method 200, the post-ventricular atrial refractory period could be adjusted in relation to the mean R-FFT duration determined at step 600.

At step 617, ventricular sensitivity is adjusted in relation to the average T-wave amplitude calculated at step 600. In the preferred embodiment, the ventricular sensitivity will be:

(1) increased by one programmable setting if the mean T-wave amplitude is less than 40% of the current ventricular sensitivity setting, (2) decreased by one programmable setting if the mean T-wave amplitude is greater than 80% of the current ventricular sensitivity setting, or (3) unchanged if the mean T-wave amplitude is between 40% and 80% of the current ventricular sensitivity setting.

Furthermore, the ventricular sensitivity is only increased or decreased when it remains within a pre-defined range bounded by a maximum and minimum setting. If the T-wave was not detected by method 250, the ventricular sensitivity is set to a default value, which may be a nominal setting stored in memory 94, typically 2 millivolts, or it may remain unchanged from the last setting in effect prior to the initiation of method 250.

At decision step 618, the subroutine 500 determines if an adjustment to the ventricular sensitivity has been made. If so, the subroutine 500 returns to step 254 of method 250 (step 619) to collect data for another N cardiac cycles, where N is the desired number of measurements to be collected and stored in memory 94 each time method 250 is enabled, before stability is verified and sensing parameters are adjusted. In this way, the method 250 is continuously repeated until the ventricular sensitivity needs no further adjustment.

Once the ventricular sensitivity no longer needs adjustment, either because it is already at its highest or lowest level allowed or it does not need to be changed according to criteria (3) above, subroutine 500 is terminated at step 620. Thus, Method 250 has completed the automatic adjustment of the ventricular sensing parameters and the post-ventricular atrial refractory period, and these parameters will remain unchanged until the next time method 250 is enabled by microprocessor 60.

Thus, an implantable cardiac stimulation device and method for reliably and accurately detecting the onset and end of cardiac events, namely R-waves, T-waves, FFR-waves and FFT-waves is provided. Furthermore, a method is provided for automatically adjusting sensing parameters, specifically atrial sensitivity, ventricular sensitivity, ventricular refractory, post-ventricular atrial refractory period (PVARP), and post-ventricular atrial blanking period (PVAB), based on the detection of the onset and end of normal sinus cardiac events. This automatic adjustment of stimulation parameters based on the accurate temporal measurement of cardiac events improves the performance of the cardiac stimulation device in reliably sensing and pacing the heart. One skilled in the art will appreciate that the present invention can be practiced by other than the described embodiments, which are presented for the purposes of illustration and not limitation.

What is claimed is:

1. A method of automatically adjusting a cardiac sensing parameter, comprising:

sensing the occurrence of a cardiac signal;

sampling the sensed cardiac signal to generate samples therefrom;

determining an onset and an end of the sensed cardiac signal from the samples;

determining the duration and amplitude of the cardiac signal; and verifying the stability of the cardiac signal, wherein if stability is verified, calculating the cardiac sensing parameter based on the duration and amplitude of the cardiac signal.

2. The method according to claim 1, wherein calculating the sensing parameter comprises calculating a ventricular sensitivity.

3. The method according to claim 1, wherein calculating the sensing parameter comprises calculating an atrial sensitivity.

4. The method according to claim 1, wherein calculating the sensing parameter comprises calculating a post-ventricular atrial blanking period (PVAB).

5. The method according to claim 1, wherein calculating the sensing parameter comprises calculating a ventricular refractory period (VREF).

6. The method according to claim 1, wherein calculating the sensing parameter comprises calculating a post-ventricular atrial refractory period (PVARP).

7. The method according to claim 1, wherein sensing the occurrence of the cardiac signal comprises sensing the occurrence of any one or more of: an atrial signal, a ventricular signal, or a combined atrial and ventricular signal.

8. The method according to claim 7, wherein sensing the occurrence of the cardiac signal comprises sensing the occurrence of any one or more of: a P-wave, R-wave, or a T-wave.

9. The method according to claim 1, wherein determining the duration of the sensed cardiac signal comprises measuring the length of time between the onset and the end of the sensed cardiac signal.

10. The method according to claim 9, wherein determining the amplitude of the sensed cardiac signal comprises measuring a maximum absolute amplitude of the samples between the onset and the end of the cardiac signal.

11. The method according to claim 10, wherein sensing the occurrence of the cardiac signal comprises sensing the occurrence of any one or more of: a P-wave, a R-wave, a T-wave, a far-field R-wave, a far-field T-wave, or an evoked response;

wherein determining the duration of the sensed cardiac signal comprises measuring the length of time between the onset and the end of any one or more of: the P-wave, the R-wave, the T-wave, the far-field R-wave, the far-field T-wave, or the evoked response; and wherein determining the amplitude of any one or more of: the P-wave, the R-wave, the T-wave, the far-field R-wave, the far-field T-wave, or the evoked response, comprises measuring the maximum absolute amplitude of the sample between the onset and the end of any one or more of: the P-wave, the R-wave, the T-wave, the far-field R-wave, the far-field T-wave, or the evoked response.

12. The method according to claim 10, wherein verifying the stability of the sensed signal comprises:

measuring a mean and a mean variance of the duration of any one or more of: the P-wave, the R-wave, the T-wave, the far-field R-wave, the far-field T-wave, or the evoked response;

measuring a mean and a mean variance of the amplitude of any one or more of: the P-wave, the R-wave, the T-wave, the far-field R-wave, the far-field T-wave, or the evoked response; and determining if the mean variances of the duration and amplitude of any one or more of: the P-wave, the R-wave, the T-wave, the far-field R-wave, the far-field T-wave, or the evoked response, are less than predetermined percentages of the means of the duration and amplitude, respectively.

13. The method according to claim 12, wherein stability is verified if the mean variance of the duration (RT duration) between the onset of the R-wave and the end of the T-wave is less than a predetermined percentage of the mean of the duration (RT duration).

14. The method according to claim 12, stability is verified if the mean variance of the maximum absolute amplitude of the T-wave is less than a predetermined percentage of the mean of the maximum absolute amplitude of the T-wave.

15. The method according to claim 12, wherein verifying the stability of the sensed signal comprises verifying the stability based on measurements made over three or more consecutive cardiac cycles.

16. The method according to claim 13, wherein calculating the sensing parameter comprises calculating a ventricular refractory period (VREF) according to the following equation:

$$VREF = RT\ duration + \Delta,$$

where $\Delta$ is a safety margin that varies between approximately 0 and a preset value.

17. The method according to claim 13, wherein calculating the sensing parameter comprises calculating a post-ventricular atrial refractory period (PVARP) according to the following equation:

$$PVARP = RT\ duration + \sigma,$$

where $\sigma$ is a predetermined value that is greater than, or equal to zero.

18. The method according to claim 13, wherein calculating the sensing parameter comprises calculating a post-ventricular atrial blanking period (PVAB) according to the following equation:

$$PVAB = R\text{-}FFR\ duration + \square.$$

where R-FFR duration is an average duration measured between the onset of the R-wave and the end of the far-field R-wave, and $\square$ is any one of: a mean variance of the duration (R-FFR duration) or a predetermined value that is greater than, or equal to zero.

19. The method according to claim 1, wherein calculating the cardiac sensing parameter comprises calculating a mean and a mean variance of the duration of the sensed cardiac signal.

20. The method according to claim 19, wherein verifying stability if the mean variance of the duration of the sensed cardiac signal is less than a predetermined percentage of the mean of the duration of the sensed cardiac signal.

21. A device for automatically adjusting a cardiac sensing parameter, comprising:

a sensor circuit that senses the occurrence of a cardiac signal;

a sampler, connected to the sensor circuit, to sample a sensed cardiac signal to generate samples therefrom;

a controller, connected to the sampler, to determine an onset and an end of the sensed cardiac signal from the samples, to determine the duration and amplitude of the sensed cardiac signal, and to verify the stability of the sensed signal; and wherein if stability is verified, the controller is operative to calculate the cardiac sensing parameter based on the duration and amplitude of the sensed cardiac signal.

22. The device according to claim 21, wherein the sensing parameter comprises any one or more of:

a ventricular sensitivity;

an atrial sensitivity;

a post-ventricular atrial blanking period (PVAB);

a ventricular refractory period (VREF); or a post-ventricular atrial refractory period (PVARP).

23. The device according to claim 22, wherein the cardiac signal is any one or more of: an atrial signal, a ventricular signal, or a combined atrial and ventricular signal.

24. The device according to claim 23, wherein the cardiac signal is any one or more of: a P-wave, R-wave, a T-wave, a far-field R-wave, a far-field T-wave, or an evoked response.

25. The device according to claim 24, wherein the controller calculates a mean and a mean variance of the duration of the cardiac signal; and wherein the duration of the cardiac signal is the length of time between the onset and the end of the cardiac signal.

26. The device according to claim 25, wherein the amplitude of the cardiac signal is a maximum absolute amplitude of the samples between the onset and the end of the cardiac signal.

27. The device according to claim 26, wherein the controller verifies the stability of the signal if the mean variance of the duration of the cardiac signal is less than a predetermined percentage of the mean of the duration of the cardiac signal.

28. The device according to claim 27, wherein the controller determines the duration of the sensed cardiac signal by measuring the length of time between the onset and the end of any one or more of: the P-wave, the R-wave, the T-wave, the far-field R-wave, the far-field T-wave, or the evoked response; and wherein the controller further determines the amplitude of any one or more of: the P-wave, the R-wave, the T-wave, the far-field R-wave, the far-field T-wave, or the evoked response, by measuring the maximum absolute amplitude of the sample between the onset and the end of any one or more of: the P-wave, the R-wave, the T-wave, the far-field R-wave, the far-field T-wave, or the evoked response.

29. The device according to claim 28, wherein the controller verifies the stability of the sensed signal by:

measuring a mean and a mean variance of the duration of any one or more of: the P-wave, the R-wave, the T-wave, the far-field R-wave, the far-field T-wave, or the evoked response;

measuring a mean and a mean variance of the amplitude of any one or more of: the P-wave, the R-wave, the T-wave, the far-field R-wave, the far-field T-wave, or the evoked response; and determining if the mean variances of the duration and amplitude of any one or more of: the P-wave, the R-wave, the T-wave, the far-field R-wave, the far-field T-wave, or the evoked response, are less than predetermined percentages of the means of the duration and amplitude, respectively.

30. The device according to claim 29, wherein the controller verifies stability if any one or more of the following conditions is satisfied:

(1) the mean variance of the duration (RT duration) between the onset of the R-wave and the end of the T-wave is less than a predetermined percentage of the mean of the duration (RT duration); or (2) the mean variance of the maximum absolute amplitude of the T-wave is less than a predetermined percentage of the mean of the maximum absolute amplitude of the T-wave.

31. The device according to claim 30, wherein the controller calculates the sensing parameter by one or more of the following ways:

(1) calculating a ventricular refractory period (VREF) according to the following equation:

$$VREF = RT \text{ duration} + \Delta,$$

where $\Delta$ is a safety margin that varies between approximately 0 and a preset value;

(2) calculating a post-ventricular atrial refractory period (PVARP) according to the following equation:

$$PVARP = RT \text{ duration} + \sigma,$$

where $\sigma$ is a predetermined value that is greater than, or equal to zero; or (3) calculating a post-ventricular atrial blanking period (PVAB) according to the following equation:

$$PVAB = R\text{-}FFR \text{ duration} + \square.$$

where R-FFR duration is an average duration measured between the onset of the R-wave and the end of the far-field R-wave, and $\square$ is any one of: a mean variance of the duration (R-FFR duration) or a predetermined value that is greater than, or equal to zero.

32. A device for automatically adjusting a cardiac sensing parameter, comprising:

means for sensing the occurrence of a cardiac signal;

means for sampling a sensed cardiac signal to generate samples therefrom;

means for determining an onset and an end of the sensed cardiac signal from the samples, for determining the duration and amplitude of the sensed cardiac signal, and for verifying the stability of the sensed signal; and means for calculating the cardiac sensing parameter based on the duration and amplitude of the sensed cardiac signal if stability is verified.

33. The device according to claim 32, wherein the sensing parameter comprises any one or more of: a ventricular sensitivity; an atrial sensitivity; a post-ventricular atrial blanking period (PVAB); a ventricular refractory period (VREF); or a post-ventricular atrial refractory period (PVARP);

wherein the cardiac signal is any one or more of: an atrial signal, a ventricular signal, or a combined atrial and ventricular signal; and wherein the cardiac signal is any one or more of: a P-wave, R-wave, a T-wave, a far-field R-wave, a far-field T-wave, or an evoked response.

* * * * *